(12) United States Patent  
Legaspi et al.

(10) Patent No.: US 8,096,985 B2
(45) Date of Patent: Jan. 17, 2012

(54) DEFLECTABLE GUIDE

(75) Inventors: Marlone Legaspi, Fremont, CA (US);
Huu Nguyen, San Jose, CA (US);
Eugene Serina, Union City, CA (US)

(73) Assignee: Guided Delivery Systems Inc., Santa Clara, CA (US)

( * ) Notice: Subject to any disclaimer, the term of this patent is extended or adjusted under 35 U.S.C. 154(b) by 0 days.

(21) Appl. No.: 12/437,495

(22) Filed: May 7, 2009

(65) Prior Publication Data

US 2009/0287187 A1 Nov. 19, 2009

Related U.S. Application Data

(60) Provisional application No. 61/051,292, filed on May 7, 2008, provisional application No. 61/160,670, filed on Mar. 16, 2009.

(51) Int. Cl.
*A61M 25/00* (2006.01)

(52) U.S. Cl. ......... 604/525; 604/523; 604/532; 604/528

(58) Field of Classification Search ............... 604/95.04, 604/523–5, 93.01, 510, 528, 530, 532; 600/585, 600/114, 434, 435, 433, 467; 607/122, 125
See application file for complete search history.

(56) References Cited

U.S. PATENT DOCUMENTS

| 3,656,185 | A | 4/1972 | Carpentier |
|---|---|---|---|
| 4,042,979 | A | 8/1977 | Angell |
| 4,044,765 | A | 8/1977 | Kline |
| 4,290,151 | A | 9/1981 | Massana |
| 4,489,446 | A | 12/1984 | Reed |
| 4,576,772 | A | 3/1986 | Carpenter |
| 4,817,613 | A | 4/1989 | Jaraczewski et al. |
| 4,898,591 | A | 2/1990 | Jang et al. |
| 5,037,404 | A | 8/1991 | Gold et al. |
| 5,057,092 | A | 10/1991 | Webster, Jr. |
| 5,064,431 | A | 11/1991 | Gilbertson et al. |
| 5,125,909 | A | 6/1992 | Heimberger |
| 5,152,744 | A * | 10/1992 | Krause et al. ................ 604/22 |
| 5,158,540 | A | 10/1992 | Wijay et al. |
| 5,163,431 | A | 11/1992 | Griep |
| 5,254,107 | A | 10/1993 | Soltesz |
| D345,419 | S | 3/1994 | Horrigan et al. |

(Continued)

FOREIGN PATENT DOCUMENTS

WO    WO-94/03227 A1    2/1994

(Continued)

OTHER PUBLICATIONS

International Search Report mailed on Jul. 6, 2009 for PCT Patent Application No. PCT/US2009/043195, filed on May 7, 2009, 1 page.

(Continued)

*Primary Examiner* — Kevin Sirmons
*Assistant Examiner* — Catherine N Witczak
(74) *Attorney, Agent, or Firm* — Morrison & Foerster LLP

(57) ABSTRACT

Described herein are devices and methods for guide catheters having one or more regions of increased flexibility. A flexibility region comprises one tubular segment of the guide catheter with a non-linear longitudinal seam between two non-concentric layers of material having different durometers. A non-linear seam, such as a zig-zag or sinusoidal configuration, permits controlled compression of lower durometer material between portions of higher durometer material.

14 Claims, 19 Drawing Sheets

U.S. PATENT DOCUMENTS

| | | |
|---|---|---|
| 5,324,298 A | 6/1994 | Phillips et al. |
| 5,348,536 A | 9/1994 | Young et al. |
| 5,381,782 A | 1/1995 | DeLaRama et al. |
| 5,399,164 A | 3/1995 | Snoke et al. |
| 5,445,625 A | 8/1995 | Voda |
| 5,527,323 A | 6/1996 | Jervis et al. |
| 5,542,924 A | 8/1996 | Snoke et al. |
| 5,569,218 A | 10/1996 | Berg |
| 5,571,215 A | 11/1996 | Sterman et al. |
| 5,624,397 A | 4/1997 | Snoke et al. |
| 5,640,955 A | 6/1997 | Ockuly et al. |
| 5,658,263 A | 8/1997 | Dang et al. |
| 5,701,905 A | 12/1997 | Esch |
| 5,718,725 A | 2/1998 | Sterman et al. |
| 5,735,290 A | 4/1998 | Sterman et al. |
| 5,769,830 A | 6/1998 | Parker |
| 5,817,107 A | 10/1998 | Schaller |
| 5,833,632 A | 11/1998 | Jacobsen et al. |
| 5,868,733 A | 2/1999 | Ockuly et al. |
| 5,897,537 A | 4/1999 | Berg et al. |
| 5,911,715 A | 6/1999 | Berg et al. |
| 5,961,440 A | 10/1999 | Schweich, Jr. et al. |
| 5,971,975 A | 10/1999 | Mills et al. |
| 5,976,120 A | 11/1999 | Chow et al. |
| 6,050,936 A | 4/2000 | Schweich, Jr. et al. |
| 6,125,852 A | 10/2000 | Stevens et al. |
| 6,159,187 A | 12/2000 | Park et al. |
| 6,162,168 A | 12/2000 | Schweich, Jr. et al. |
| 6,168,588 B1 * | 1/2001 | Wilson .......................... 604/525 |
| 6,199,262 B1 * | 3/2001 | Martin ...................... 29/525.15 |
| 6,203,531 B1 | 3/2001 | Ockuly et al. |
| 6,591,472 B1 | 7/2003 | Noone et al. |
| 6,595,983 B2 | 7/2003 | Voda |
| 6,610,087 B1 | 8/2003 | Zarbatany et al. |
| 6,645,160 B1 | 11/2003 | Heesch |
| 6,648,874 B2 | 11/2003 | Parisi et al. |
| 6,695,793 B2 | 2/2004 | Brennan et al. |
| 6,749,560 B1 | 6/2004 | Konstorum et al. |
| 6,793,618 B2 | 9/2004 | Schweich, Jr. et al. |
| 6,814,744 B2 | 11/2004 | Yang et al. |
| 6,858,024 B1 | 2/2005 | Berg et al. |
| 6,871,085 B2 | 3/2005 | Sommer |
| 6,908,424 B2 | 6/2005 | Mortier et al. |
| 6,989,025 B2 | 1/2006 | Burgmeier et al. |
| 7,090,683 B2 | 8/2006 | Brock et al. |
| 7,125,421 B2 | 10/2006 | Tremulis et al. |
| 7,189,199 B2 | 3/2007 | McCarthy et al. |
| 7,226,467 B2 | 6/2007 | Lucatero et al. |
| 7,232,422 B2 | 6/2007 | Gibson et al. |
| 7,276,062 B2 | 10/2007 | McDaniel et al. |
| 7,306,585 B2 | 12/2007 | Ross |
| 7,326,231 B2 | 2/2008 | Phillips et al. |
| 7,452,325 B2 | 11/2008 | Schaller |
| 7,618,449 B2 | 11/2009 | Tremulis et al. |
| 2003/0032979 A1 | 2/2003 | Mortier et al. |
| 2003/0171736 A1 | 9/2003 | Bon |
| 2003/0233105 A1 | 12/2003 | Gayton |
| 2004/0193191 A1 | 9/2004 | Starksen et al. |
| 2004/0243102 A1 | 12/2004 | Berg et al. |
| 2004/0243227 A1 | 12/2004 | Starksen et al. |
| 2005/0054919 A1 | 3/2005 | Spear et al. |
| 2005/0055087 A1 | 3/2005 | Starksen |
| 2005/0107811 A1 | 5/2005 | Starksen et al. |
| 2005/0273138 A1 | 12/2005 | To et al. |
| 2006/0058817 A1 | 3/2006 | Starksen et al. |
| 2006/0089618 A1 | 4/2006 | McFerran et al. |
| 2006/0122633 A1 | 6/2006 | To et al. |
| 2006/0129188 A1 | 6/2006 | Starksen et al. |
| 2006/0190030 A1 | 8/2006 | To et al. |
| 2007/0055206 A1 | 3/2007 | To et al. |
| 2007/0060880 A1 | 3/2007 | Gregorich et al. |
| 2007/0135830 A1 | 6/2007 | Schaeffer |
| 2008/0172035 A1 | 7/2008 | Starksen et al. |
| 2008/0294177 A1 | 11/2008 | To et al. |
| 2009/0182417 A1 | 7/2009 | Tremulis et al. |
| 2009/0276038 A1 | 11/2009 | Tremulis et al. |

FOREIGN PATENT DOCUMENTS

| | | |
|---|---|---|
| WO | WO-95/15715 A1 | 6/1995 |
| WO | WO-96/39942 A1 | 12/1996 |
| WO | WO-97/27799 A1 | 8/1997 |
| WO | WO-97/27807 A1 | 8/1997 |
| WO | WO-03/105667 A2 | 12/2003 |
| WO | WO-03/105667 A3 | 12/2003 |
| WO | WO-2008/028135 A2 | 3/2008 |
| WO | WO-2008/028135 A3 | 3/2008 |

OTHER PUBLICATIONS

U.S. Appl. No. 12/366,553, filed Feb. 5, 2009, by Nguyen et al.

Written Opinion of the International Searching Authority mailed on Jul. 6, 2009 for PCT Patent Application No. PCT/US2009/043195, filed on May 7, 2009, 5 pages.

International Preliminary Report on Patentability mailed on Nov. 18, 2010 for PCT Patent Application No. PCT/US2009/043195, filed on May 7, 2009, 8 pages.

Extended European Search Report mailed on Sep. 6, 2011, for EP Patent Application No. 09743698.4, filed on May 7, 2009, 7 pages.

* cited by examiner

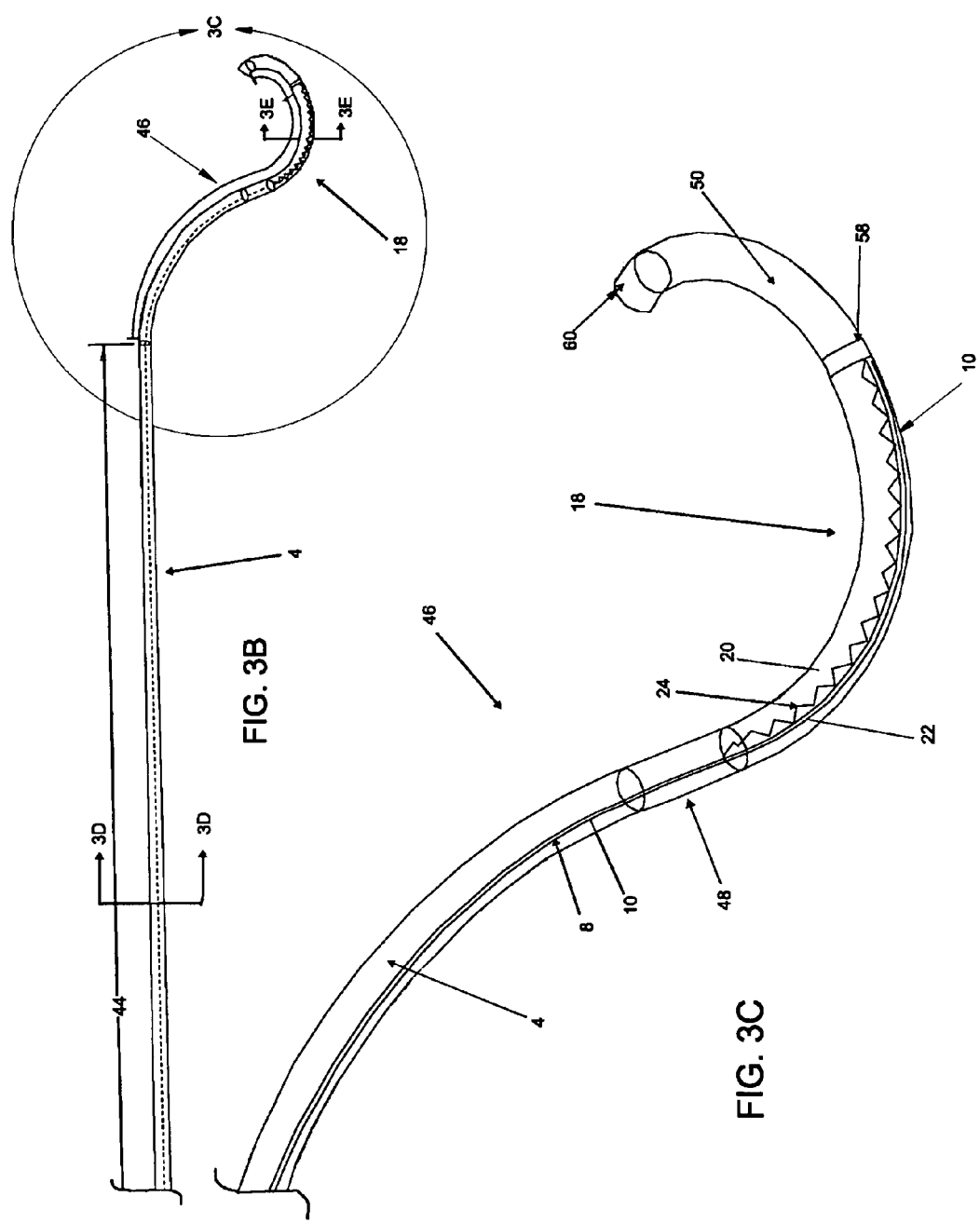

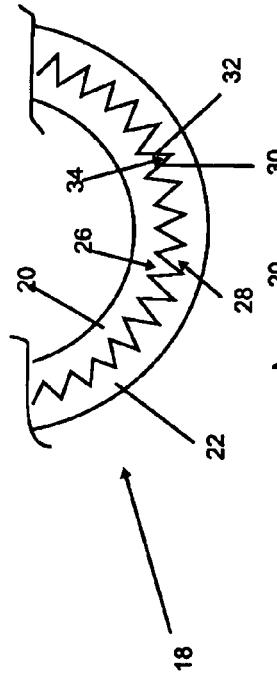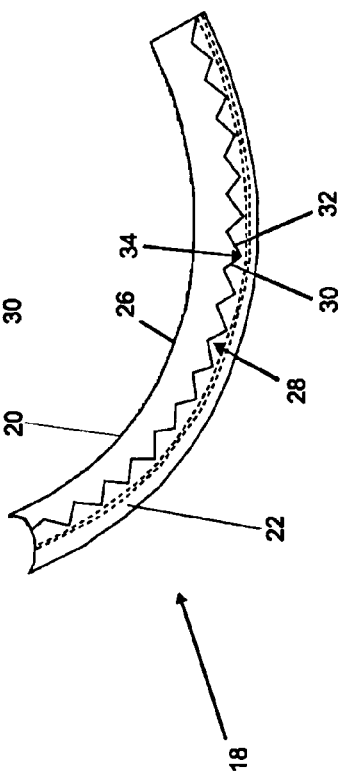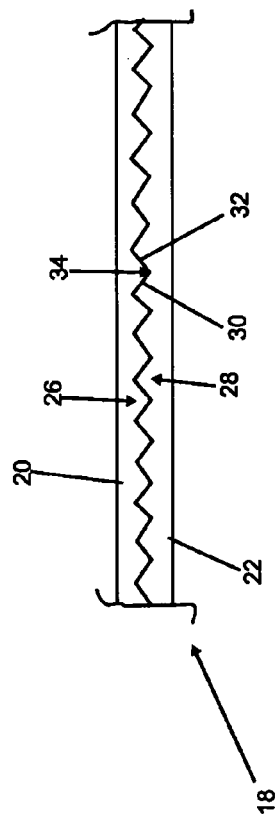

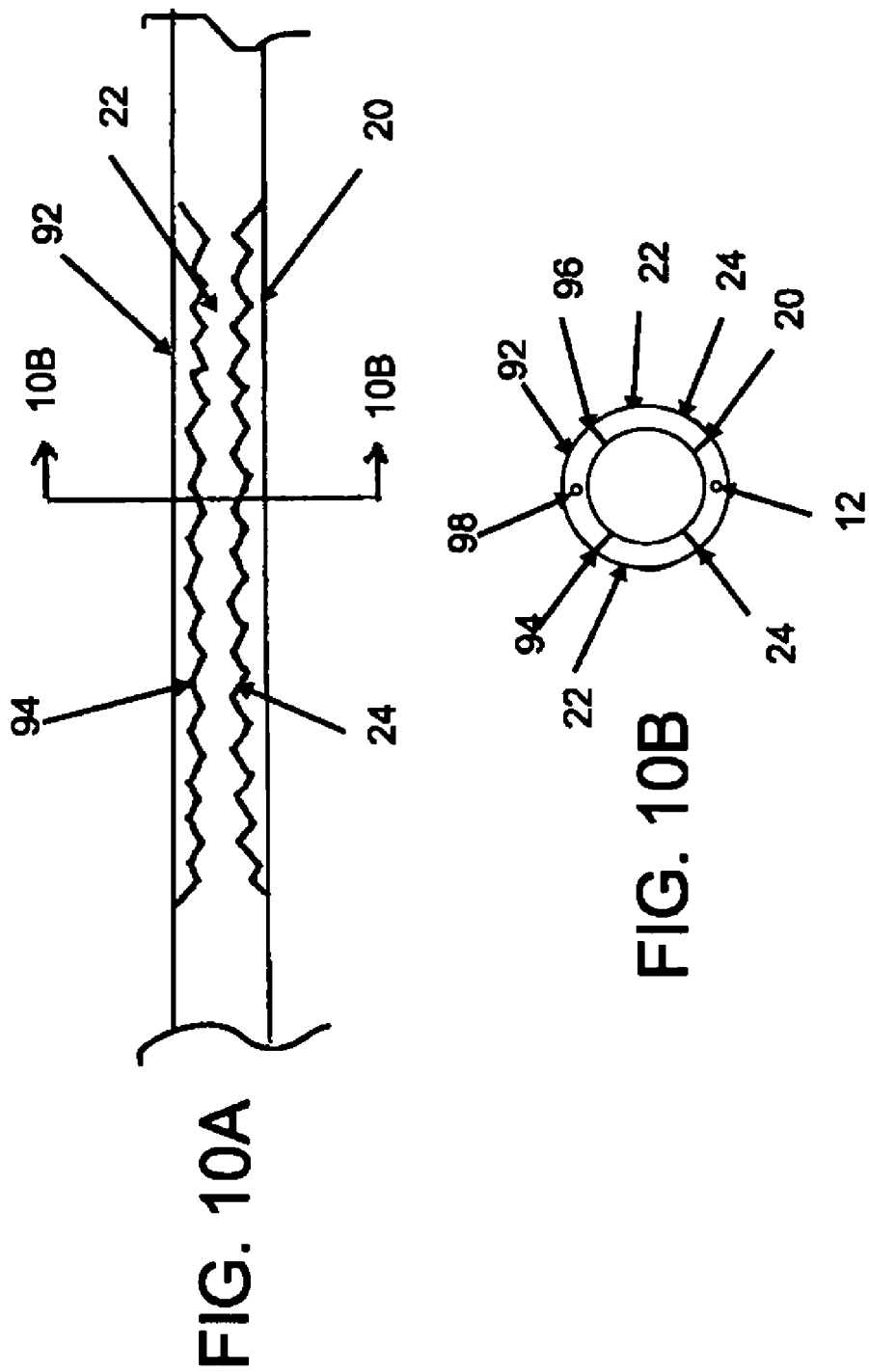

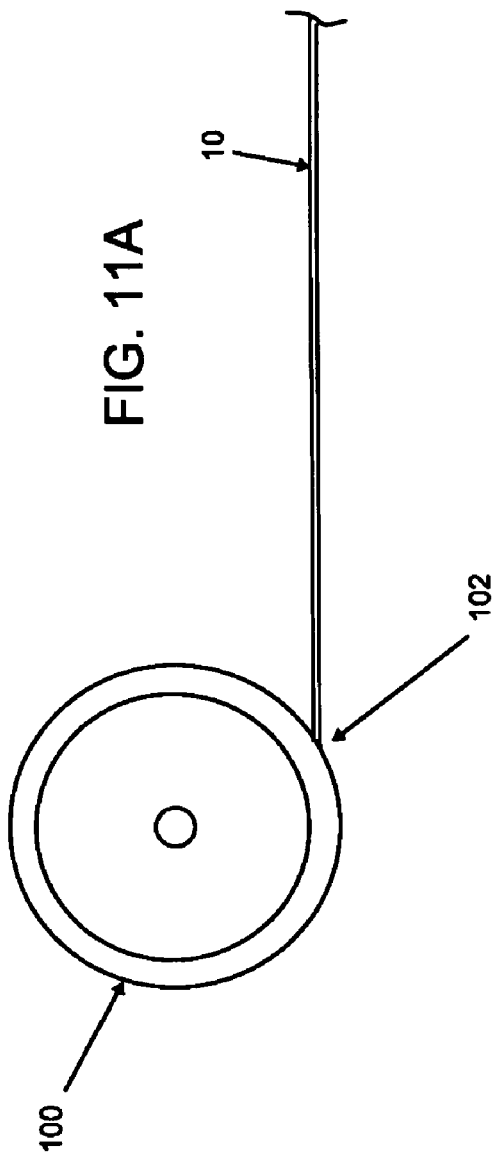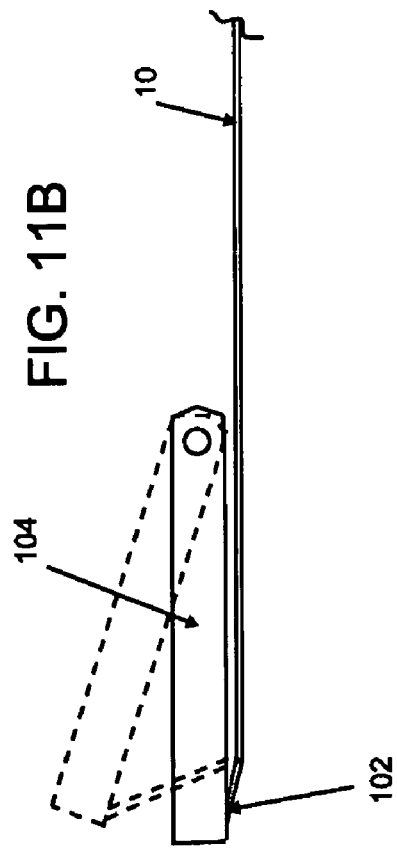

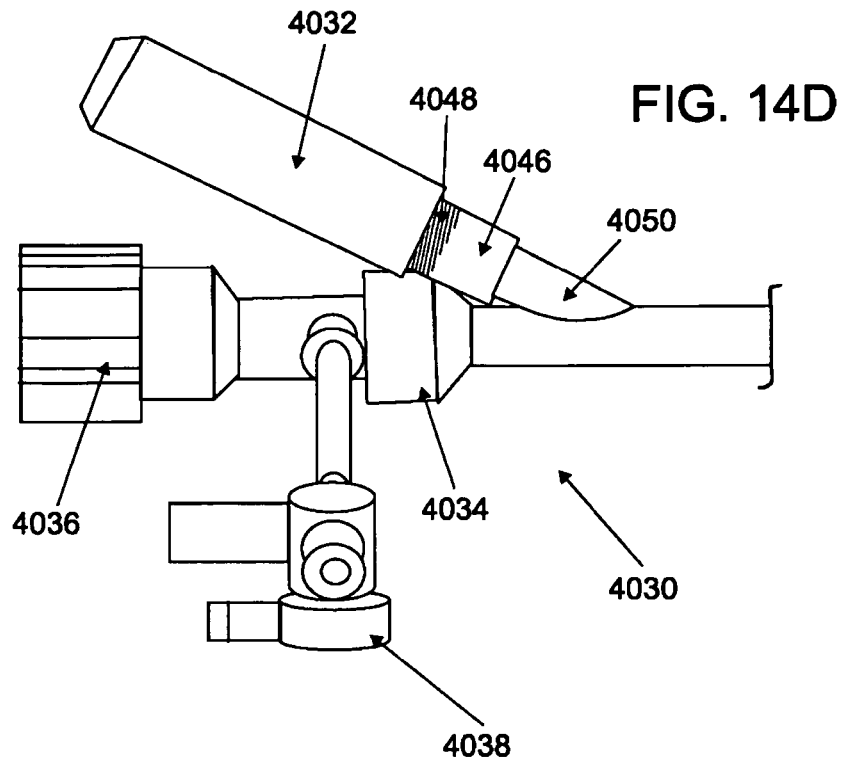
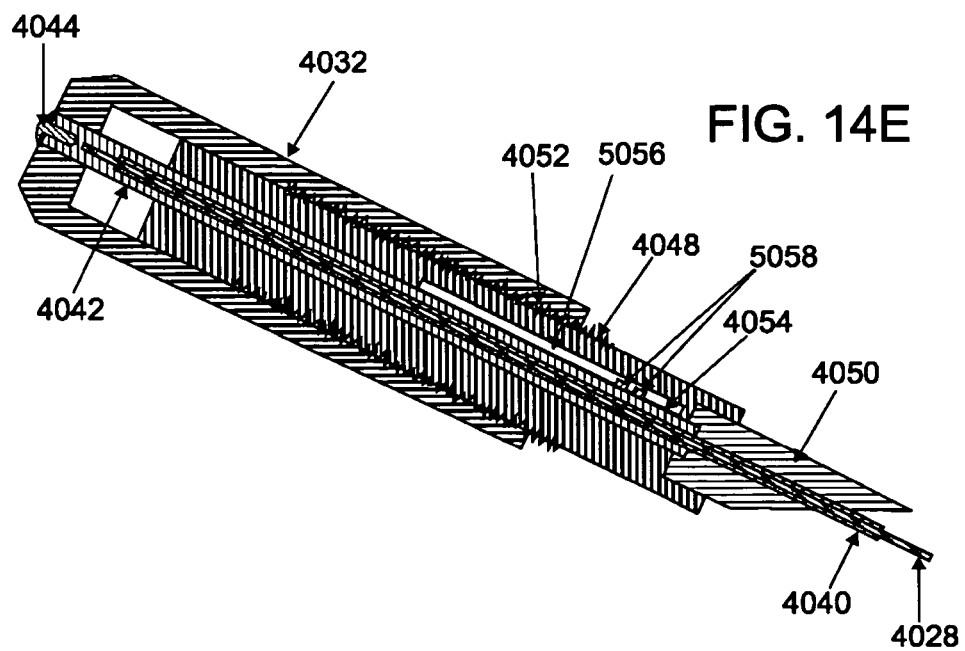

DEFLECTABLE GUIDE

CROSS-REFERENCE TO RELATED APPLICATIONS

The present application claims priority under 35 U.S.C. §119(e) to U.S. Provisional Application No. 61/051,292, filed on May 7, 2008, and to Provisional Application No. 61/160,670 filed on Mar. 16, 2009, which are hereby incorporated by reference in their entirety.

BACKGROUND

Guide catheters are used in a variety of therapeutic and diagnostic medical procedures to facilitate insertion of instruments and implantable components. Guide catheters often comprise a rigid material or support structure to provide the torqueability and pushability characteristics that facilitate passage of the guide catheter to a particular site. With the stiffer material or support structure, the responsiveness of the distal portion of the guide catheter to manipulation of the proximal portion of the guide catheter typically improves. A flexible material, however, permits the guide catheter to navigate around tight bends and other hard-to-reach places. Although some guide catheters may be generically configured for use with a variety of procedures, some guide catheters have a particular length, stiffness and distal tip shape adapted for access to a specific tissue or organ.

BRIEF SUMMARY

Described herein are devices and methods for guide catheters having one or more deformation zones. In one embodiment, a deformation zone comprises a tubular segment of the guide catheter with a longitudinal interface between two non-concentric sections of material having different durometers. The longitudinal interface may be linear or non-linear. A non-linear interface between the two sections of material, such as a zig-zag or sinusoidal interface, may permit controlled deformation of the lower durometer material between portions of higher durometer material. This deformation may include stretching and/or compression. In some embodiments, the deformation zone reduces the buckling of higher durometer material that may interfere with insertion or withdrawal of catheters or instruments from the lumen of the guide catheter.

In some embodiments, the guide catheter may further comprise a pull wire or ribbon which is secured to the guide catheter distal to the deformation zone and is slidable along a pull wire lumen through a proximal actuator. The pull wire may be used to control deflection of the guide catheter at the deformation zone. The actuator may be, for example, a rotatable knob, a pivoting lever or a slider. The actuator may comprise a bias element, such as a spring or other elastic element, that may be used to bias the pull wire toward a particular position. The actuator may also comprise a locking mechanism that may be used to maintain the pull wire in one or more positions.

In some embodiments, a catheter is provided, comprising a deformation zone comprising a proximal end, a distal end, a longitudinal length and a longitudinal axis therebetween, a lower durometer segment, a higher durometer segment, and a first longitudinal interface between the lower durometer segment and the higher durometer segment, wherein the first interface has a length greater than the longitudinal length of the deformation zone. The lower durometer segment and/or the higher durometer segment may comprise a polymeric material. The first interface may have a non-linear configuration, including but not limited to a zig-zag configuration, or intercalating portions of the lower durometer segment and the higher durometer segment. In some embodiments, the deformation zone may further comprise a second interface between the lower durometer segment and the higher durometer segment, wherein the second interface is separate from the first interface. In one embodiment, the second interface may have a length greater than the longitudinal length of the deformation zone. In another embodiment, the deformation zone may have a first configuration and a second configuration, wherein the second configuration has an increased bend compared to the first configuration. The second configuration may be a curved configuration having a lesser curvature and a greater curvature, and wherein the lower durometer segment is located along the lesser curvature. In some further embodiments, the catheter may further comprise a means for controlling bending of the deformation zone. In some instances, the higher durometer segment has an angular width of at least about 45 degrees on an axial cross-section of the deformation zone. In other embodiments, the lower durometer segment has an angular width of at least about 90 degrees or at least about 180 degrees on the axial cross-section of the deformation zone.

In another embodiment, a catheter is provided, comprising a deformation zone comprising a proximal end, a distal end, a longitudinal length therebetween, a first polymeric layer comprising a proximal edge, a distal edge, a first lateral edge and a second lateral edge, and a second polymeric layer comprising a proximal edge, a distal edge, a first lateral edge and a second lateral edge, wherein the first polymeric material has a lower durometer than the second polymeric material, and wherein the first lateral edge of the first polymeric layer is joined to at least a portion of the second lateral edge of the second polymeric layer, and wherein the second lateral edge of the first polymeric layer is joined to at least a portion of the first lateral edge of the second polymeric layer.

In another embodiment, a method for treating a patient is provided, comprising providing a catheter having a lower durometer region comprising at least one compressible portion and a greater durometer region comprising at least two constricting portions in an alternating configuration with the last least one compressible portion, bending the catheter such that the at least two constricting portions of the higher durometer region compresses the at least one compressible portion of the lower durometer region, and passing a tubular body down a passageway of the catheter.

In still another embodiment, a system for treating a patient is provided, comprising a guide catheter comprising a longitudinal axis, a guide lumen, and at least one deformation zone, the at least one deformation zone comprising two segments of polymeric material of different durometers and a longitudinal interface therebetween with respect to the longitudinal axis of the guide catheter, a tunnel catheter comprising a tubular body with a tunnel lumen, wherein the tubular body is configured for insertion into the guide lumen of the guide catheter, and a delivery catheter comprising an anchor retaining cavity and an anchor delivery mechanism, wherein the delivery catheter is configured for insertion into the tunnel lumen of the tunnel catheter. The tubular body of the tunnel catheter may further comprise a plurality of delivery apertures in communication with the tunnel lumen. In some embodiments, the longitudinal configuration between the two segments of polymeric material comprises a reciprocating longitudinal configuration.

In one embodiment, a method for accessing a cardiac region of a patient is provided, comprising providing a steerable guide catheter comprising two polymeric materials forming a longitudinal interface therebetween, where the two polymeric materials comprise a first polymeric material having a first durometer and a second polymeric material having second durometer greater than the first durometer, passing the steerable guide catheter through a cardiac valve orifice, compressing the first polymeric material with the second polymeric material about the longitudinal interface, and steering the steerable guide catheter into a subvalvular region adjacent the cardiac valve orifice.

BRIEF DESCRIPTION OF THE DRAWINGS

The structure and method of using the invention will be better understood with the following detailed description, along with the accompanying illustrations, in which:

FIG. 3B is a detailed view of the catheter body of the deflectable guide catheter in FIG. 3A;

FIG. 3C is a detailed view of the distal end of the deflectable guide catheter in FIGS. 3A and 3B;

FIGS. 4A to 4C are schematic representations of a deformation zone in various configurations;

FIG. 10A illustrates another embodiment of a deformable zone of a deflectable guide catheter;

FIG. 10B represents a cross section of the deformable zone depicted in FIG. 10A;

FIG. 11A is a schematic representation of one embodiment of a steering mechanism;

FIG. 11B is a schematic representation of another embodiment of a steering mechanism;

FIG. 14D is a detailed superior elevational view of the proximal end of the guide catheter; and FIG. 14E is a longitudinal cross sectional view of the steering mechanism of the guide catheter.

DETAILED DESCRIPTION OF THE INVENTION

Figure 1:
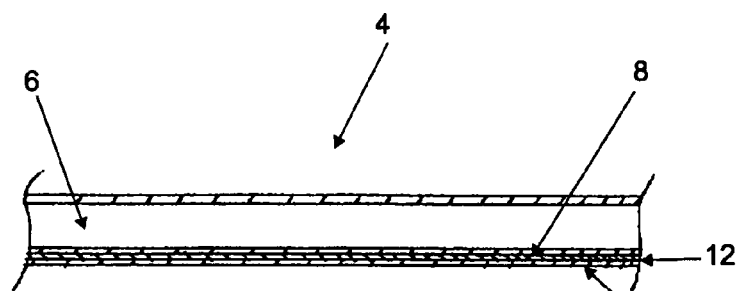
FIG. 1 is a cross-sectional view of a catheter body with a pull wire.
Figure 2A:
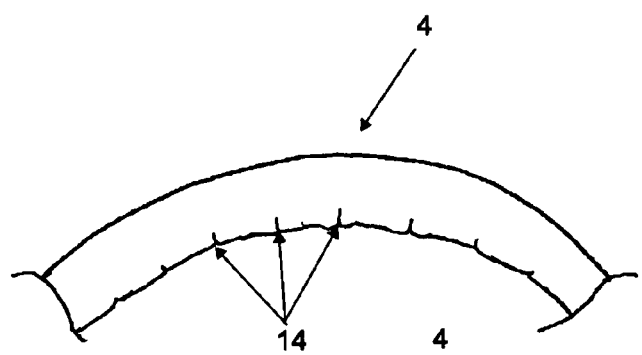
FIGS. 2A and 2B are schematic side elevation and cross sectional views of the catheter body of FIG. 1 in a bent configuration, respectively.
Figure 2B:
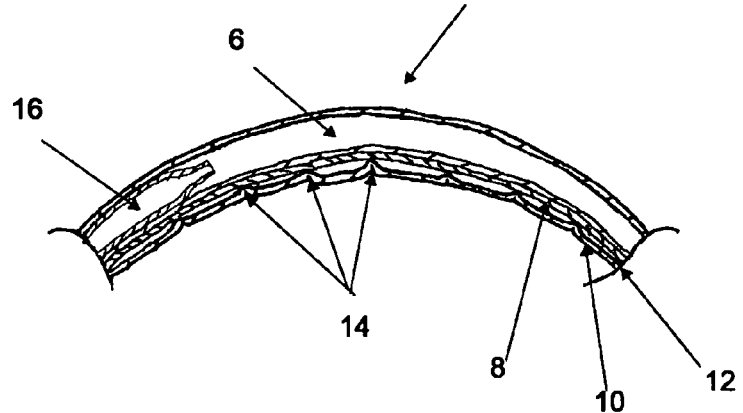

The ease of inserting a catheter to a body location may be influenced by a number of catheter characteristics. While a catheter made from stiffer materials may improve its user responsiveness relating torqueability and pushability over longer insertion distances, stiffer catheter materials may affect the catheter's maneuverability through tight anatomical bends. In some cases, catheter maneuverability may be improved by using a steering mechanism to position the catheter tip in the desired orientation or direction. FIG. 1 illustrates one example of a steerable catheter segment, comprising a tubular catheter body 4 with one or more conduits 6 and a pull lumen 8 containing a pull member 10. Typically, pull member 10 is attached distally to catheter body 4 such that, when pulled proximally, pull member 10 will cause catheter body 4 to bend, as shown in FIG. 2A. While a steering mechanism 12 may improve the bending range of stiffer catheter materials, such materials may cause creases 14 or other discontinuities in catheter body 4 when bent, as illustrated in FIG. 2A. Further, such creases 14 may impair the ability to pass instruments 16 or components down conduit 6, as shown in the cross-sectional view of FIG. 2B.

Figure 3A:
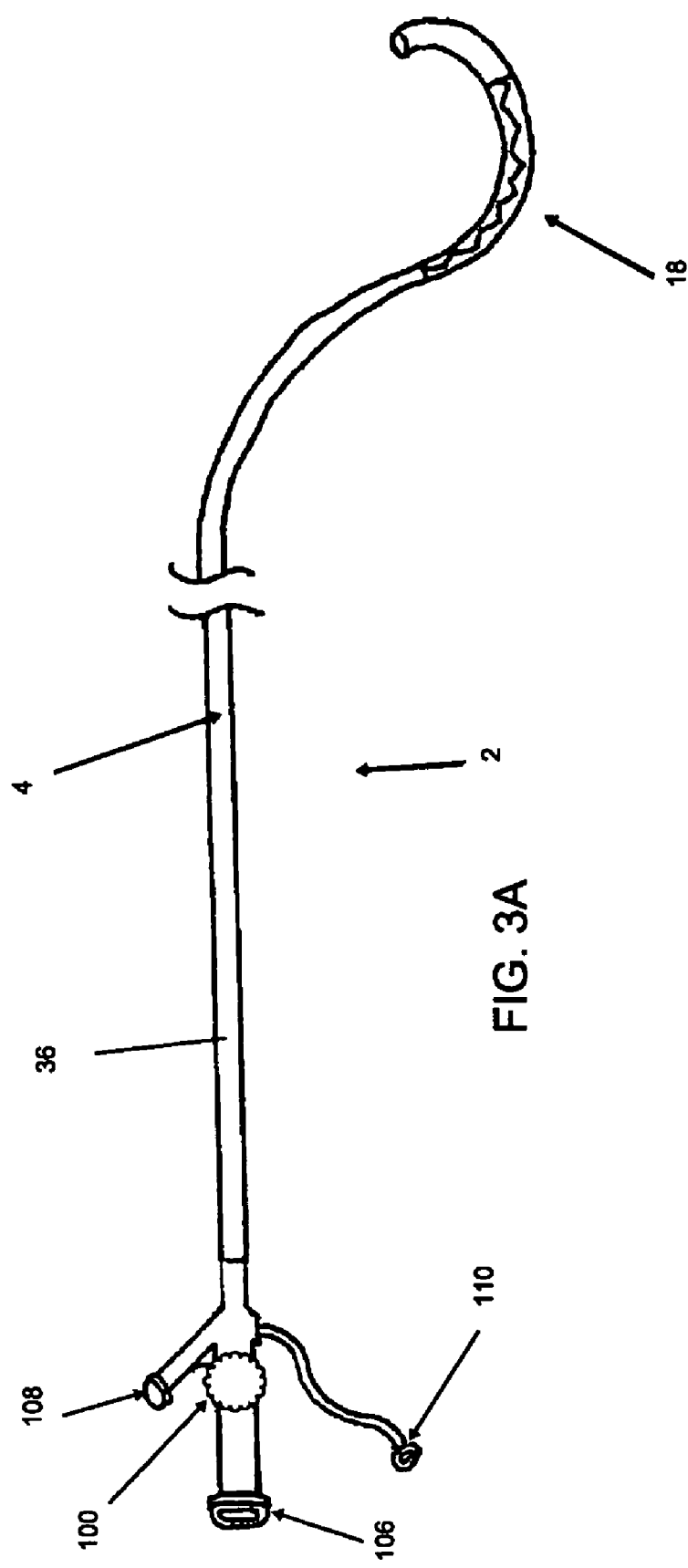
FIG. 3A illustrates one embodiment of a deflectable guide catheter.

In one embodiment, shown in FIG. 3A, a steerable catheter 2 with one or more deformation zones 18 is provided. Referring to FIG. 3C, deformation zone 18 may comprise a segment of catheter body 4 comprising a first layer segment 20 and a second layer segment 22 arranged with a longitudinal interface 24 therebetween. First layer segment 20 and second layer segment 22 comprise different physical characteristics such that first layer segment 20 is able to compress or stretch when flexed. In some embodiments, first layer segment 20 comprises a material having a lower durometer than second layer segment 22. In embodiments where deformation zone 18 is formed by two layer segments, two longitudinal interfaces are formed where the two lateral borders of each layer segment form a longitudinal interface with the complementary lateral border of the other layer segment. In other embodiments, first layer segment 20 may comprise a structural geometry, such as surface cuts or grooves, that may help control or distribute flexion forces to reduce impingement of any conduits.

In some embodiments, longitudinal interface 24 generally has a linear or simple curve configuration similar to the longitudinal axis of catheter body 4. In the embodiment depicted in FIG. 3C, however, longitudinal interface 24 is oriented with a similar axis as the longitudinal axis of catheter body 4 but with a zig-zag configuration. Referring to FIG. 4A, the zig-zag configuration of longitudinal interface 24 comprises alternating protruding sections of first layer segment 20 and second layer segment 22. These alternating protruding sections, shown in this particular embodiment as triangular sections 26 and 28, have side lengths 30 and 32 which meet to form an angle 34 between two adjacent sides 30. In FIG. 4C, when deformation zone 18 is straightened from its configuration in FIG. 4B, triangular sections 26 of first layer segment 20 are stretched or relieved of compression as angle 34 is increased by the angular separation of triangular sections 28 of second layer segment 22. In contrast, as depicted in FIG. 4A, when deformation zone 18 is acutely bent relative to FIG. 4A, triangular sections 26 of first layer segment 20 are compressed as angle 34 is decreased by the angular reduction of triangular sections 28 of second layer segment 22. In some embodiments of the invention, the zig-zag pattern may reduce the incidence or degree of pinching or creasing of any conduits in catheter body 4 by controlling compression of the lower durometer material in first layer segment 20 with the protruding sections 28 of the higher durometer material in second layer segment 22. Further, in some embodiments, the zig-zag pattern may provide a more even distribution of the forces along the full length of deformation zone 20, compared to simple linear or simple curved interfaces. In some embodiments, second layer segment 22 may be contiguous with tubular body 36.

In one embodiment, deformation zone 18 is configured to bend from about 180 degrees to about 30 degrees, about 180 degrees to about 45 degrees in some embodiments, and about 180 degrees to about 90 degrees in other embodiments. In some embodiments, deformation zone 18 is able to bend in two or more directions and/or two or more planes from its straight or base configurations. The range of bending in two or more directions or planes need not be symmetrical with respect to the straight or base configurations. The base configuration need not be linear. Various embodiments of non-linear base configurations are discussed later.

In some embodiments, catheter body 4 may have a total length of about 20 cm to about 200 cm or more, about 60 cm to about 160 cm in other embodiments, and about 100 cm to about 120 cm in still other embodiments. In one embodiment, catheter body 4 may have an outer diameter of about 5 F to about 34 F, in other embodiments about 8 F to about 20 F, and about 12 F to about 16 F in some embodiments. In some embodiments of the invention, conduit 6 is sized to accept catheters or instruments with a size of about 3 F to about 30 F, in a few embodiments about 6 F to about 16 F, and about 8 F to about 12 F in other embodiments.

Catheter body 4 can be formed from any of a variety of materials. Examples of suitable materials include but are not limited to polymers, such as polyether-block co-polyamide polymers, copolyester elastomers, thermoset polymers, polyolefins (e.g., polypropylene or polyethylene, including high-density polyethylene and low-density polyethylene), polytetrafluoroethylene, ethylene vinyl acetate, polyamides, polyimides, polyurethanes, polyvinyl chloride (PVC, fluoropolymers (e.g., fluorinated ethylene propylene, perfluoroalkoxy (PFA) polymer, polyvinylidenefluoride, etc.), polyetheretherketones (PEEKs), Polyetherketoneketones (PEKKs) and silicones. Examples of polyamides that may be included in tunnel catheter (410) include Nylon 6 (e.g., Zytel® HTN high performance polyamides from DuPont™), Nylon 11 (e.g., Rilsan® B polyamides from Arkema Inc.), and Nylon 12 (e.g., Grilamid® polyamides from EMS-Grivory, Rilsan® A polyamides from Arkema Inc., and Vestamid® polyamides from Degussa Corp.). In one embodiment, catheter body 4 comprises PEBAX®, a polyether block amide (PEBA) available from ATOMCHEM POLYMERS of Birdsboro, Pa. First layer segment 20 and second layer segment 22 may comprise different materials or the same general type of material but with different durometers. In some embodiments, the durometer of the material may range from about 5 D to about 72 D, sometimes about 35 D to about 72 D, other times about 35 D to about 55 D, or about 55 D to about 72 D. Catheter body 4 may comprise one or more layers, and sometimes two or more layers. Although FIGS. 3A to 3C depict first layer segment 20 and second layer segment 22 as forming the outermost layer of deformation zone 18, in other embodiments of the invention, these layer segments 20 and 22 may be covered by one or more other layers or reinforcing structures. Catheter body 4 need not comprise the same number of polymeric layer along its entire length.

Catheter body 4 and/or conduit 6 may be reinforced (e.g., with tubular or arcuate braiding, circular loops, helical structures, or longitudinal supports). The reinforcing structure or structures may comprise a metallic material or a non-metallic material. Metallic materials that may be used include but are not limited to stainless steel such as 316L, nitinol and cobalt-chromium.

Referring back to the specific embodiment depicted in FIGS. 3A and 3B, catheter body 4 may comprise a proximal section 44 and a distal section 46. Referring to FIG. 3D, in this specific embodiment, proximal section 44 comprises a tubular body 36 and a single conduit 6 optionally lined with a coating 38. Typically, proximal section 44 has a linear configuration, but in other embodiments, proximal section 44 may have a non-linear configuration, including angled and curved configurations or combinations thereof. In some embodiments, tubular body 36 optionally comprises one or more reinforcement structures 40. In some embodiments, tubular body 36 may comprise PEBAX 72D, coating 38 may comprise PTFE and reinforcement structure 40 may comprise a tubular stainless steel wire braid surrounding conduit 6. Proximal section 44 further comprises a pull lumen 8 and pull member 10 within the wall of proximal section 44. Pull lumen 8 and/or pull member 10 may also be coated with a lubricious coating such as PTFE. In further embodiments, pull lumen 8 may be reinforced with a material such as polyimide. As shown in FIG. 4D, in some embodiments of the invention, the wall thickness of catheter body 4 or proximal section 36 may vary along their longitudinal lengths or circumferences.

In some embodiments, distal section 46 may comprise a particular shape with optional multiple sections. For example, as shown in FIG. 3C, distal section 46 may comprise a pre-deformation section 48, a second section comprising deformation zone 18, a post-deformation section 50 and a distal tip 52. In this particular embodiment, pre-deformation section 48 comprises a curved configuration but otherwise may have similar components as proximal section 44, with a tubular body 36, conduit 6, and pull member 10 within pull lumen 8. In other embodiments of the invention, the components and features of pre-deformation section 48 may be different from proximal section 44. In this particular embodiment, distal to pre-deformation section 48 is deformation zone 18 configured with a curved configuration with a curvature opposite of pre-deformation section 48. In other embodiments of the invention, deformation zone 18 may have a linear or angled configuration, with an angular orientation from about 0 degrees to about 359 degrees with respect to pre-deformation section 48. In some embodiments, deformation zone 18 may have an angular orientation of about 0 degrees, about 15°, about 30°, about 45°, about 60°, about 75°, about 90°, about 105°, about 120°, about 135°, about 150°, about 165°, about 180°, about 195°, about 210°, about 225°, about 240°, about 255°, about 270°, about 285°, about 300°, about 315°, about 330°, or about 345°. The bending plane of deformation zone 18, however, need not be the same plane as its curved configuration and may have an angular orientation from about 0 degrees to about 359 degrees to the plane of its curved configuration. In some embodiments, the bending plane of deformation zone has an angular orientation of about In some embodiments, deformation zone 18 may have an angular orientation of about 0 degrees, about 15°, about 30°, about 45°, about 60°, about 75°, about 90°, about 105°, about 120°, about 135°, about 150°, about 165°, about 180°, about 195°, about 210°, about 225°, about 240°, about 255°, about 270°, about 285°, about 300°, about 315°, about 330°, or about 345° with respect to the plane of its curved configuration.

In some embodiments, deformation zone 18 may have a longitudinal length of about 0.75 inches to about 10 inches, some embodiments about 1 inch to about 4 inches or more, and in other embodiments about 1.5 inches to about 2 inches in length. In some embodiments of the invention, deformation zone 18 may have similar inner and outer diameters as described for catheter body 4, but in other embodiments, deformation zone 18, the inner diameter of conduit 6 may be smaller or larger and the outer diameter of tubular body 36 may be smaller or larger.

Figure 3E:
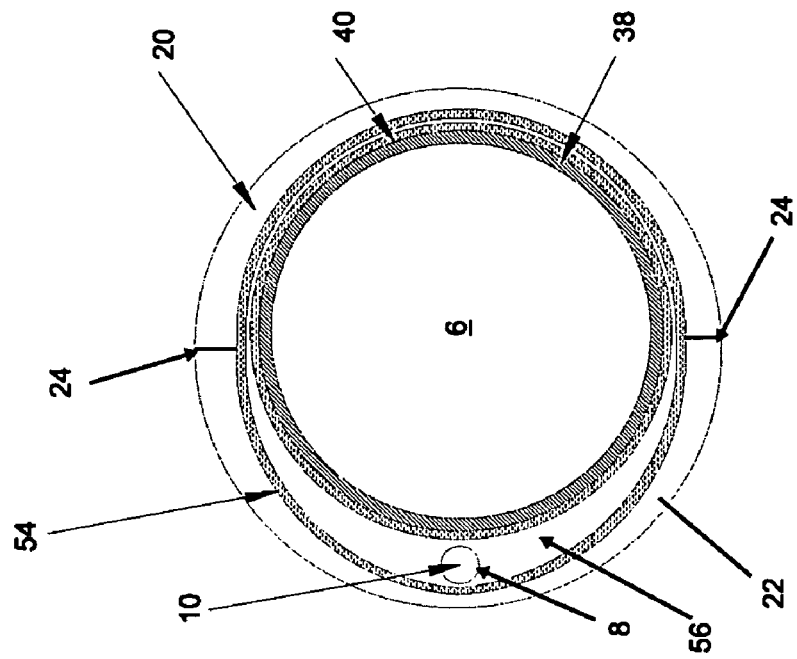
FIGS. 3D and 3E are various cross sectional views of the catheter body of FIG. 3B.
Figure 3D:
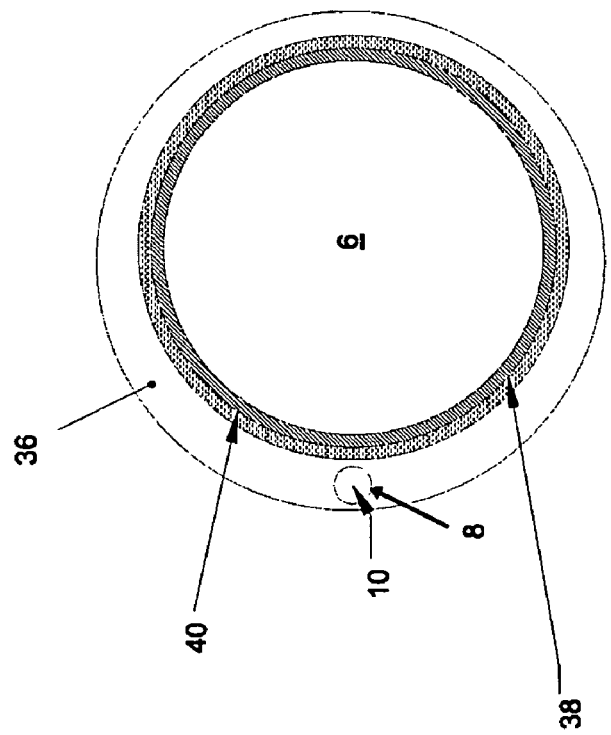

Referring to FIG. 3E, in this specific embodiment, deformation zone 18 comprises an outer layer 42 formed by first layer segment 20 and second layer segment 22. Conduit 6, pull lumen 8, pull member 10 and reinforcement structure 40 are arranged in deformation zone 18 similar to proximal section 44, except that a second reinforcement structure 54 is provided. In this embodiment, second reinforcement structure 54 comprises a second tubular stainless steel braid surrounding conduit 6 and pull lumen 8. In some embodiments, second reinforcement structure 54 may originate proximally in pre-deformation section 48 of distal section 46. The portion 56 of tubular body 36 between reinforcement structures 40 and 54 may comprise a similar material as segments 20 or 22, or a different material.

Although several embodiments depicted and described herein have a single conduit 6, in other embodiments, two or more conduits may be provided. Embodiments of the invention with multiple conduits need not have conduits with the same diameter, shape or cross-sectional area. Furthermore, any one conduit need not have the same diameter, shape or cross-sectional area along its entire length. Thus, some conduits may comprise a circular shape, but in other embodiments the conduits may be oval, square, rectangular or any other shape. As mentioned previously, in some embodiments of the invention, conduit 6 may comprise a lubricious coating, including but not limited to PTFE.

In some embodiments, catheter body 4 may also comprise one or more radio-opaque structures or materials to facilitate identification and localization of guide catheter 2 with radiographic imaging. The imaging may include but is not limited to fluoroscopy, CT imaging, MRI imaging, and intravascular ultrasound or echocardiography. The radio-opaque structures may be found along the entire length or a portion of the length of catheter body 4. In some embodiments, at least one radio-opaque structure is located at post-deformation section 50 or distal tip 60.

As mentioned previously, segments 20 and 22 may be joined at their lateral edges to form two longitudinal interfaces 24. In this specific embodiment, segment 20 comprises PEBAX 35D while segment 22 comprises PEBAX 72D. Because segments 20 and 22 in this specific embodiment have generally semi-circular configurations, longitudinal interfaces 24 have generally 180 degree opposite locations with respect to conduit 6. In other embodiments, however, deformation zone 18, interfaces 24 may be angularly closer together, or may comprise three or more interfaces 24.

Referring back to FIG. 3C, in some embodiments, distal section 46 further comprises a post-deformation section 50 distal to deformation zone 18. Post-deformation section 50 may be straight, angled or curved, or a combination thereof. Post-deformation section 50 may have a longitudinal length of about 0.25 inches to about 5 inches or more, sometimes about 0.5 inches to about 2 inches, and occasionally about 0.75 inches to about 1.25 inches. Post-deformation section 50 may comprise one or more layers. In some embodiments, post-deformation section 50 comprises the same material as one of the segments from deformation zone 18, but in other embodiments, post-deformation section 50 may comprise a material having a higher, lower or intermediate durometer. For example, in one embodiment of the invention, segments 20 and 22 of deformation zone 18 comprise PEBAX 35D and 72D, respectively, while post-deformation section 50 comprises PEBAX 55D. Post-deformation section 50 may or may not include one or more reinforcement structures. In some embodiments, the reinforcement structure may be contiguous with reinforcement structures 40 and/or 54, and in some embodiments may include a reinforcement structure different from reinforcement structures 40 and/or 54.

In some embodiments, one or more conduits from the proximal portions of catheter body 4 may pass through post-deformation section 50 or terminate within it. In embodiments of the invention with a single deformation zone and/or steering mechanism, however, pull lumen 8 and/or pull member 10 may terminate within post-deformation section 50. To facilitate the exertion of force in distal section 46 of catheter body 4, pull member 10 may comprise a distal pull structure 58. Pull member 10 may be coupled to distal pull structure 58 or be contiguous with distal pull structure 58. In the embodiment illustrated in FIG. 3C, distal pull structure 58 may comprise a ring-like structure embedded in post-deformation section 50. In alternate embodiments, distal pull structure 58 may comprise a helical winding of pull member 10 or some other wire-based configuration. Pull member 10 may comprise any of a variety of materials and structures sufficient to transmit longitudinal forces along a length of catheter body 4. Pull member 10 and distal pull structure 58 may be metallic, non-metallic or a combination thereof, including but not limited to stainless steel, nitinol, nylon or other polymeric material. In some embodiments, pull member 10 may be coated, for example, to facilitate sliding in pull lumen 8. Such coatings may include PTFE.

In some embodiments, pull member 10 may comprise a structure and a material whereby pull member 10 can exert force on catheter body 4 only when pulled. In these embodiments, catheter body 4 may have a preconfigured shape such that when the force acting on pull member 10 is released, catheter body 4 is biased to return to its preconfigured shape. In other embodiments, pull member 10 has a sufficient stiffness such that pull member 10 may also be pushed to facilitate bending of catheter body 4 in a direction generally different or opposite from the bending that occurs when pull member 10 is pulled. In other embodiments of the invention, distal pull structure 58 may be located within deformation zone 18.

As depicted in FIG. 3C, catheter body 4 may optionally comprise a distal tip 60 with a different structure or configuration relative to post-deformation section 50. In embodiments, distal tip 60 is configured as an atraumatic tip and may comprise a material and/or structure different from tubular body 36, deformation zone 18 or post-deformation section 50. In some embodiments, distal tip 60 comprises a material with a durometer equal to or lower than a material found in either deformation zone 18 or post-deformation section 50. In one specific example, distal tip 60 comprises PEBAX 35D, while post-deformation section 50 comprises PEBAX 55D, segment 20 comprises PEBAX 35D, segment 22 comprises PEBAX 72D and tubular body 36 comprises PEBAX 72D. Distal tip 60 may have a longitudinal length of about 1 mm to about 20 mm or more, sometimes about 2 mm to about 10 mm, and occasionally about 5 mm. The inner and outer diameters of distal tip 60 may be the same or different from other portions of catheter body 4.

Figure 5:
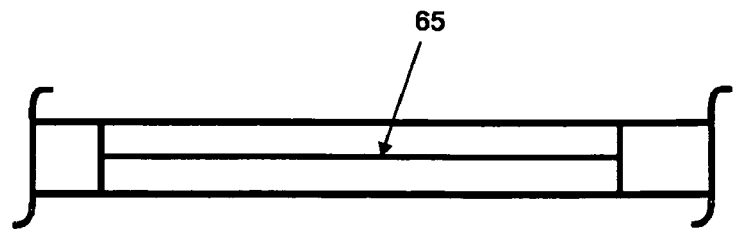
FIG. 5 represents one embodiment of the interface between two sections of catheter body material.
Figure 6A:
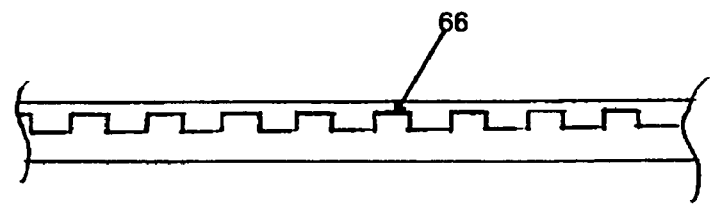
FIGS. 6A to 6D represent other embodiments of the interface between two sections of catheter body material.
Figure 6B:
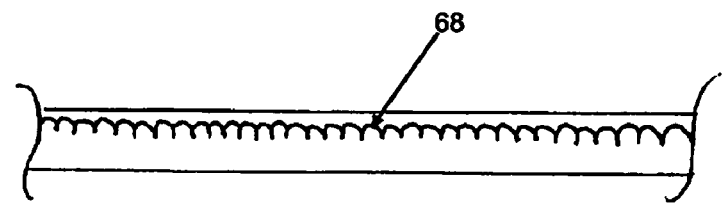
Figure 6C:
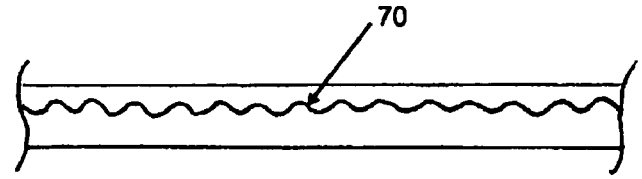
Figure 6D:
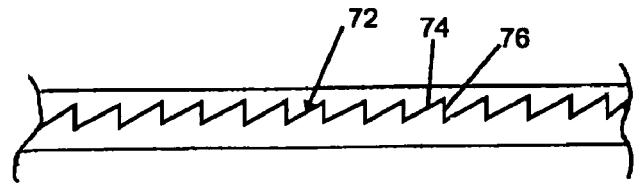

In some embodiments, interface 24 may have a relatively linear configuration 65, as depicted in FIG. 5, or a non-linear configuration other than a zig-zag pattern. For example, interface 24 may comprise a reciprocating pattern including but not limited to a square wave pattern 66, a scalloped pattern 68, and a sinusoidal pattern 70 as depicted in FIGS. 6A to 6C, respectively. As shown in FIG. 6D, the reciprocating pattern 72 need not have symmetric subsegments. In this embodiment for example, the leading edge 74 has a different length and angle as the trailing edge 76.

Figure 7A:
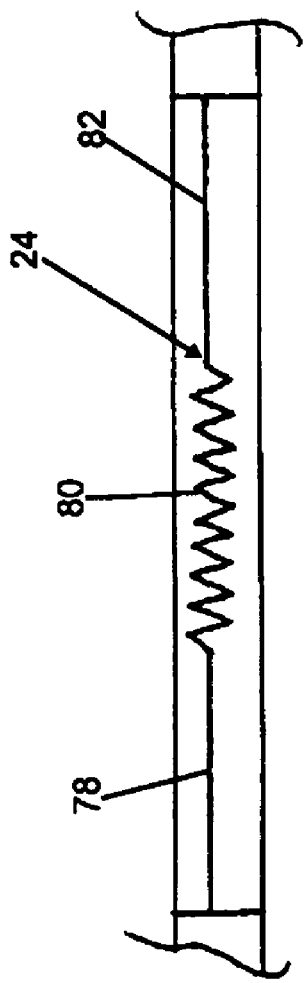
FIGS. 7A to 7C represent various embodiments of the interface between two sections of catheter body material.
Figure 7B:
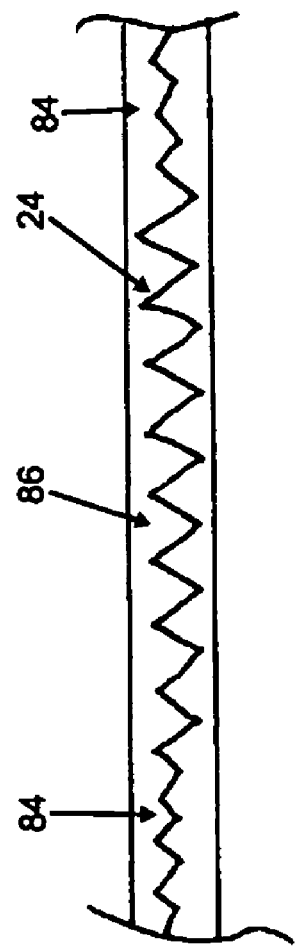
Figure 7C:
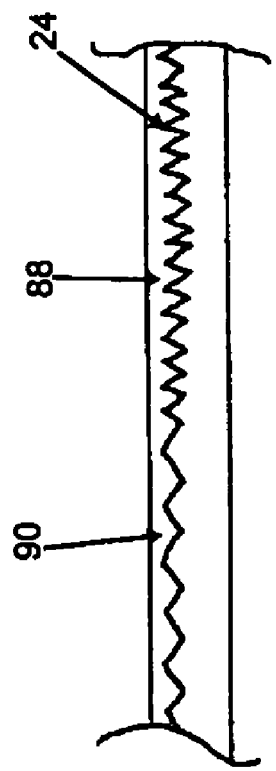

As depicted in FIGS. 7A to 7C, interface 24 need not comprise the same repeating pattern along its entire length. For example, in the embodiment depicted in FIG. 7A, interface 24 comprises a linear portion 78 followed by a zig-zag portion 80 and another linear portion 82. In another embodiment depicted in FIG. 7B, interface 24 comprises the same pattern but with sections of low and high amplitude 84 and 86, respectively. In still another embodiment shown in FIG. 7C, interface 24 comprises a pattern of similar amplitude but contains portions with relatively shorter and longer repeating lengths 88 and 90, respectively. These features may be mixed and matched to achieve the desired structural features in deformation zone 18.

Figure 8A:
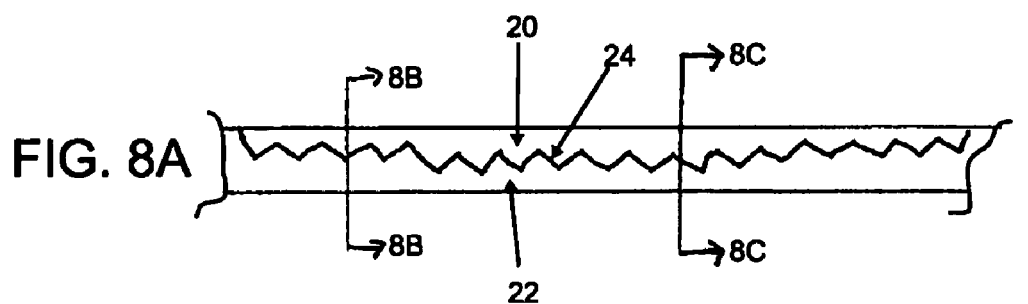
FIG. 8A illustrates one embodiment of a deformable zone of a deflectable guide catheter.
Figure 8B:
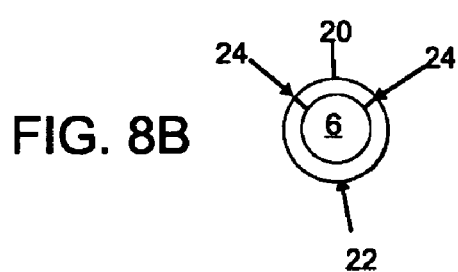
FIGS. 8B and 8C represent various cross sections of the deformable zone depicted in FIG. 8A.
Figure 8C:
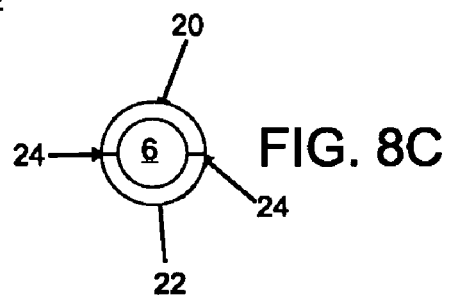
Figure 9A:
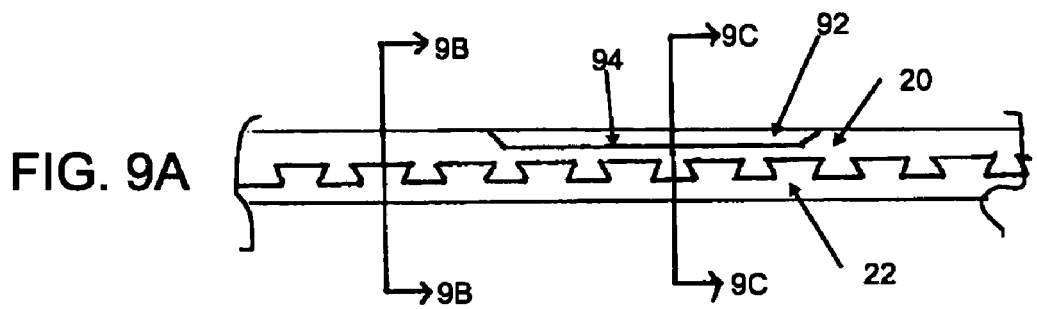
FIG. 9A illustrates another embodiment of a deformable zone of a deflectable guide catheter.
Figure 9B:
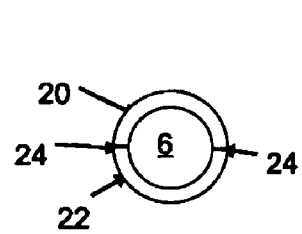
FIGS. 9B and 9C represent various cross sections of the deformable zone depicted in FIG. 9A.
Figure 9C:
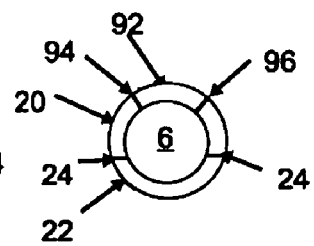

As mentioned previously, the embodiment depicted in FIGS. 3A to 3E comprises a deformation zone 18 with two similarly sized semi-circular segments 20 and 22, and two interfaces 24 about 180 degrees apart with respect to conduit 6. In other embodiments, however, segments 20 and 22 may have different sizes and shapes. In FIG. 8A, for example, segment 20 has a reduced width at one or more ends, resulting in interfaces 24 forming a narrower angle in one section (FIG. 8B) as compared to another section (FIG. 8C). In other embodiments of the invention, as depicted in FIG. 9A, the deformation zone may comprise a third layer segment 92, resulting in additional interfaces 94, 96.

In some embodiments, such as the embodiment depicted in FIGS. 3A to 3E, deformation zone 18 comprises a single steering mechanism 12, but in other embodiments, multiple pull lumens with multiple pull members may be provided. In FIG. 10A, for example, the deformation zone comprises three layer segments 20, 22 and 92 arranged to facilitate the bending of the deformation zone in opposite directions. As shown in FIG. 10B, two steering mechanisms 12 and 98 may be provided to facilitate bending in opposite directions. In other embodiments, the two or more steering mechanisms may be located about 15°, about 30°, about 45°, about 60°, about 75°, about 90°, about 105°, about 120°, about 135°, about 150°, about 165°, about 180°, about 195°, about 210°, about 225°, about 240°, about 255°, about 270°, about 285°, about 300°, about 315°, about 330°, or about 345° with respect to the plane of its curved configuration. In other embodiments of the invention, multiple steering mechanisms with different distal longitudinal terminations along the length of catheter body 4 may be provided, to facilitate along different lengths of bending. The longitudinal separation may be about 1 cm to about 50 cm or more, sometimes about 5 cm to about 20 cm, and at other times about 5 cm to about 10 cm apart.

Any of a variety of control mechanisms may be used to manipulate one or more pull members 10. In FIG. 3A, for example, a rotatable knob 100 may be provided on steering catheter 2. Referring to FIG. 11A, the proximal end 102 of pull member 10 may be attached to a rotating knob 102, or alternatively to a pivoting lever 104, as illustrated schematically in FIG. 11B. In other embodiments, pull member 10 may be manipulated by a pull ring or a slider. Steering mechanism 12 may further comprise a bias member (not shown), such as a spring or elastic member, to bias distal section 46 to a particular position. Steering mechanism may also comprise a releasable locking mechanism to maintain pull member 10 in a desired position.

In some embodiments, the knob 100 or other proximal control member is coupled to a single pull member. In other embodiments with multiple pull members, one or more control members may be provided, particularly in embodiments with multiple deformation zones, but the number of control members need not be equal to the number of pull members. In these embodiments, two or more pull members may be coupled to a single control member. For example, a knob or slider may be engaged to dual pull members with a neutral position having a relative equal or zero force acting between the two pull members. Manipulation of the knob or slide in one direction away from the neutral position will exert force on one pull member, while manipulation of the slide or knob in the other direction away from the neutral position will exert force on the other pull member. The configuration of catheter body 4 associated with the neutral position may be a linear or a non-linear configuration.

Referring back to FIG. 3A, the proximal end of guide catheter 2 may have one or more ports 106, 108 and 110. These ports may communicate with conduit 6 or other conduits of multi-conduit embodiments of the invention. In some embodiments, one or more ports may be provided to obtain blood samples, for injection of intravenous fluids, radiographic or therapeutic agents, or for the attachment of a pressure transducer. One or more ports 106, 108 and 110 may be configured with a hemostasis valve to reduce fluid or blood leakage, and/or a lock for resisting displacement of any components inserted into that port. In one embodiment, the lock is a releasable lock that can be released and re-engaged as needed. In some embodiments, the components used with a port may include one or more indicia along its length that may be used to identify the degree of insertion into guide catheter 2.

In the specific embodiment depicted in FIG. 3A, port 106 associated with conduit 6, may be configured for the insertion of a tunnel catheter or other instrument. In some embodiments, a tunnel catheter may be used in conjunction with guide catheter 2 to provide additional guidance beyond the distal end of guide catheter 2. Providing a guidance pathway using both guide catheter 2 and a tunnel catheter may be easier to position at a target site or be easier to manufacture than a single guide catheter configured to traverse the entire guidance pathway.

Figure 12A:
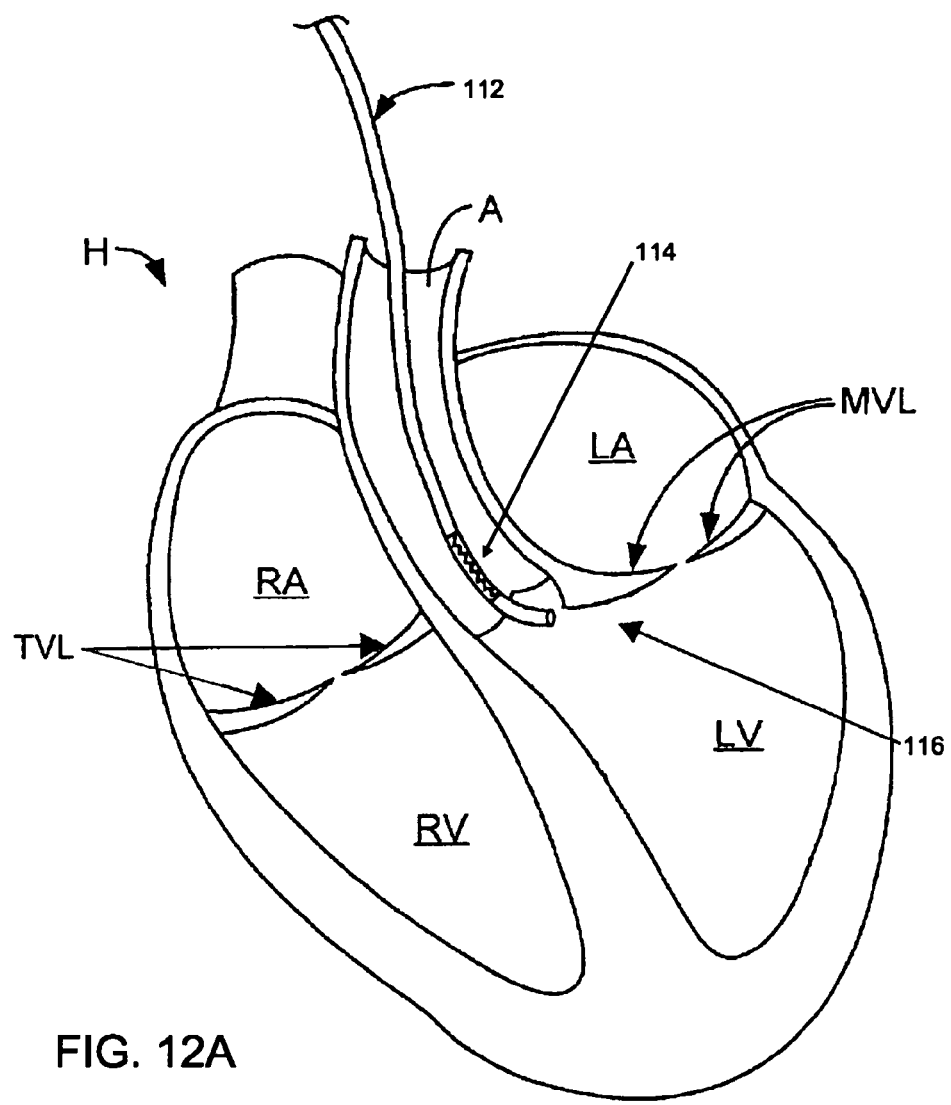
FIGS. 12A and 12B depict one embodiment of a deflectable guide catheter used to reach the subvalvular groove region of a mitral valve.
Figure 12B:
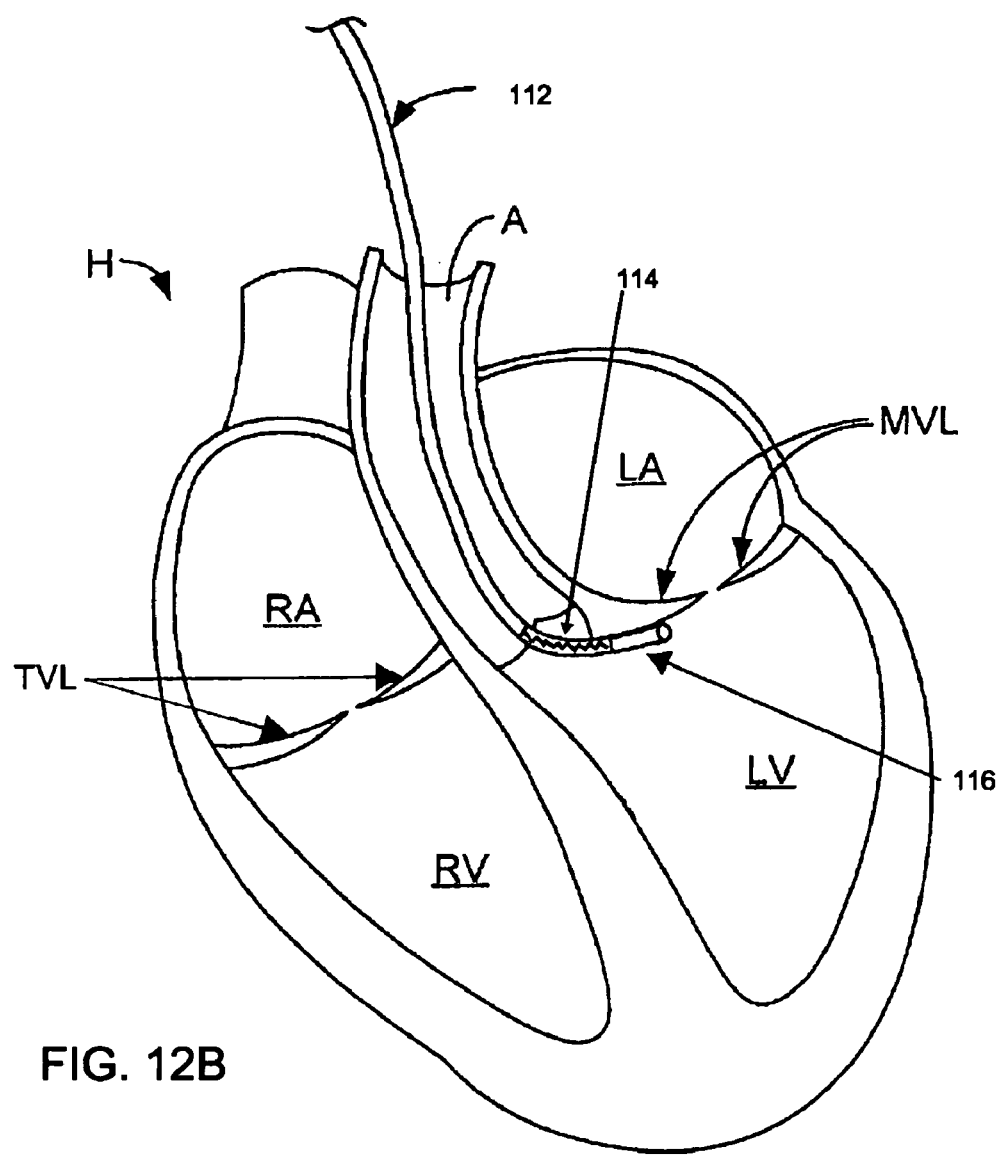
Figure 13A:
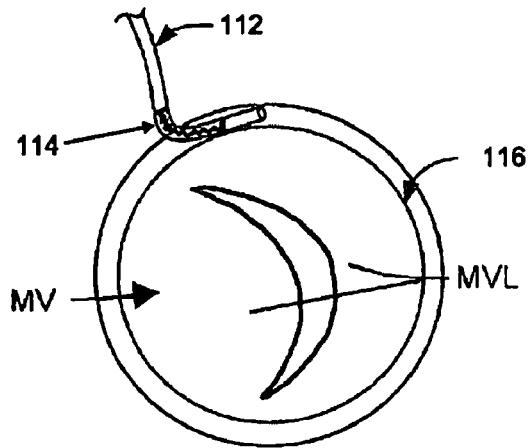
FIGS. 13A to 13E are schematic representations of a deflectable guide catheter used to implant a cinchable implant along the subvalvular region of a mitral valve.
Figure 13B:
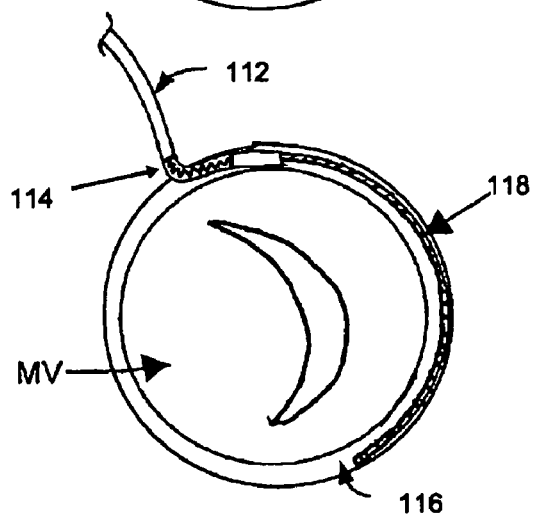
Figure 13C:
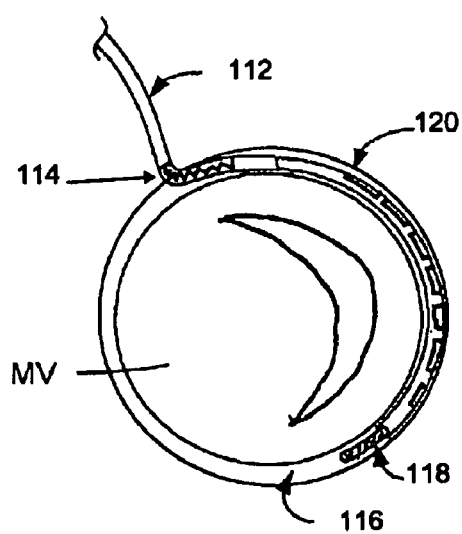
Figure 13D:
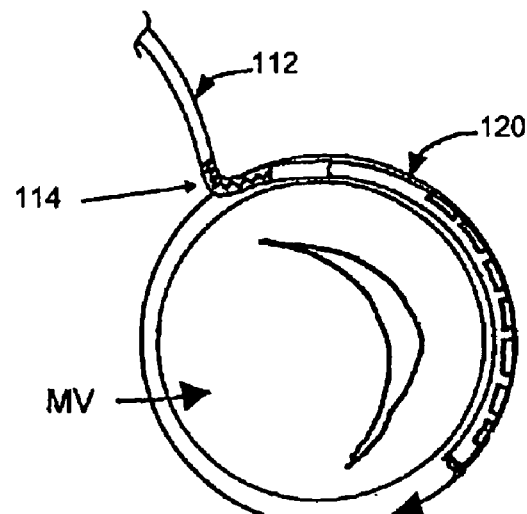
Figure 13E:
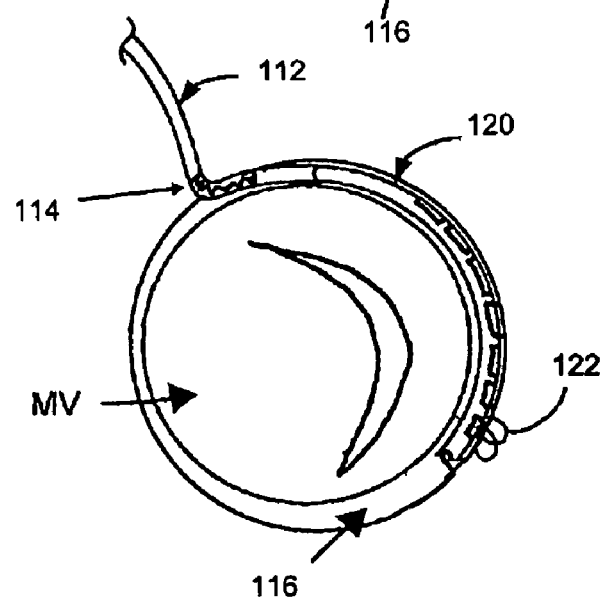

For example, FIG. 12A depicts one exemplary use of a guide catheter 112 with a deformation zone 114. Guide catheter 112 may be inserted from a peripheral vascular site and passed in a retrograde direction through the aorta A. As guide catheter 112 passes through the aortic valve, the steering mechanism of guide catheter 112 may be manipulated to bend toward the subvalvular region 116 adjacent the mitral valve leaflets MVL, as shown in FIG. 12B. Although a sharp turn may be formed in guide catheter 112 by providing a pathway from the aortic valve to the subvalvular region, instead of looping guide catheter 112 below the chordae tendinae or the apex of the left ventricle, deformation zone 18 permits controlled flexion that does not impinge or infold into the conduit provided in guide catheter.

Figure 14A:
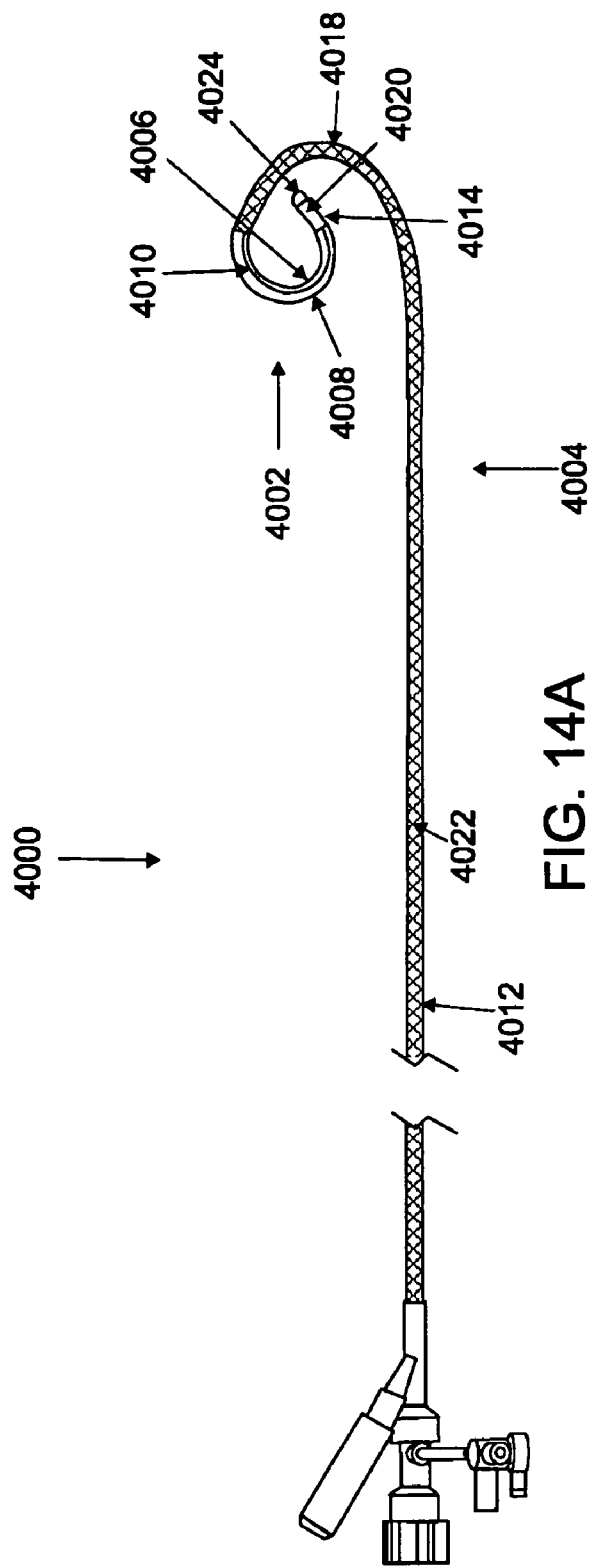
FIG. 14A is a superior elevational view of a variation of a steerable guide catheter.

In another variation, shown in FIG. 14A, the steerable catheter 4000 comprises a deformation region 4002 with a segment of the catheter body 4004 having a first layer segment 4006 and a second layer segment 4008 with a generally linear longitudinal interface 4010 therebetween. The first layer segment 4006 comprises a lower durometer material and the second layer segment 4008 comprises a higher durometer material. The catheter body 4004 may further comprise a proximal shaft 4012 and a distal shaft 4014 with respect to the deformation region 4002. The proximal shaft 4012 may comprise a tubular configuration with at least one inner lumen (not shown) that may be optionally lined with a coating. The proximal shaft 4012 may have a generally linear configuration, but in other variations, proximal shaft 4012 may have a non-linear configuration, including angled and curved sections or combinations thereof, such as the arch curve region 4018. The distal shaft 4014 may also have a linear or curved configuration, such as the valve curve region 4020 depicted in FIGS. 14B and 14C. Additional variations and methods of use for these and other deflectable guide catheters are described in U.S. Provisional Application No. 61/160,670 entitled "VISUALIZATION METHODS AND RELATED DEVICES AND KITS", filed Mar. 16, 2009, which is hereby incorporated by reference in its entirety. In some variations, the proximal shaft 4012 may comprise one or more reinforcement structures 4022, such as tubular or arcuate braiding or interweaving, circular loops, helical structures, or longitudinal supports). The reinforcement structure may comprise one or more metallic or non-metallic materials as described previously. In one example, the proximal shaft 4012 may comprise an outer layer of PEBAX 72 D, and the reinforcement structure 4022 may comprise a tubular stainless steel wire braid, which in turn may have an inner coating of PTFE. In the example of FIG. 14A, the distal shaft 4014 comprises a material having a durometer between the durometer of the first and second segments 4006 and 4008, but in other examples, the durometer may be generally equal to, less than or greater than the first and second segments 4006 and 4008, respectively. The distal shaft 4014 may also comprise an atraumatic tip 4024, which may comprise a material having lower durometer than the rest of the distal shaft 4014, or may be tapered or otherwise shaped to be more flexible or deformable. The distal shaft 4014 may comprise a linear or non-linear configuration, and may be oriented in the same or a different plane with respect to the deformation region 4002 and/or proximal shaft 4012, as shown in FIG. 14D.

Figure 14B:
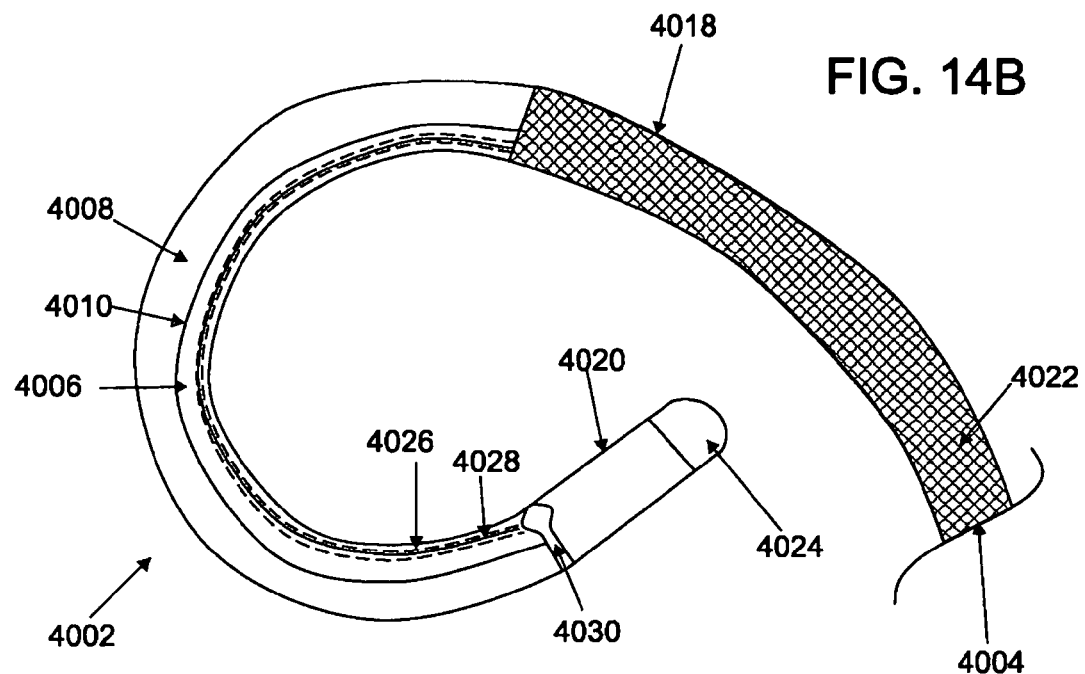
FIG. 14B is a detailed superior elevational view of the distal end of the guide catheter.
Figure 14C:
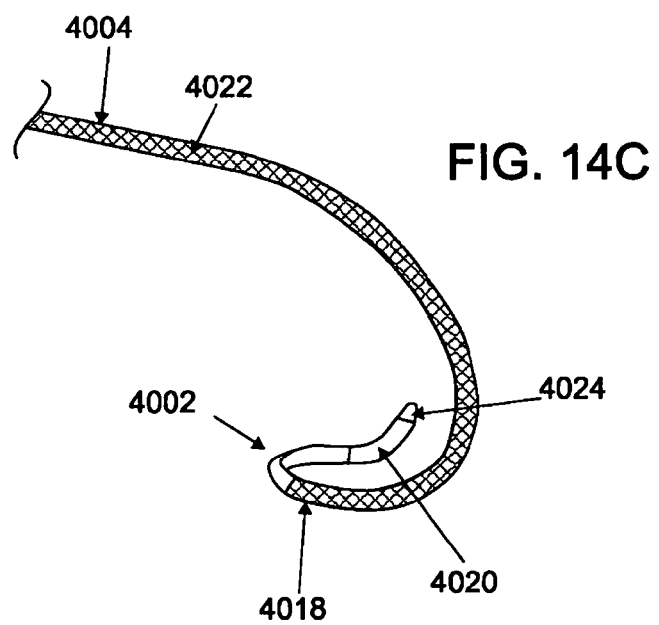
FIG. 14C is a side elevational view of the distal end of the guide catheter.

Referring to FIG. 14B, the proximal shaft 4012 may further comprise a pull lumen 4026 and a pull member 4028 within the wall of proximal shaft 4012. The pull lumen 4026 and/or pull member 4028 may also be coated with a reduced friction coating, such as PTFE. In further variations, the pull lumen 4026 may be reinforced with a material such as polyimide. The pull member 4028 may comprise any of a variety of materials, including but not limited to stainless steel, nylon, polyimide, and the like. The pull lumen 4026 and/or pull member 4028 may terminate within the deformation region 4002 or the distal shaft 4014. To facilitate the exertion of force in the distal shaft 4014 of the catheter body 4004, the pull member 4028 may comprise a distal pull structure 4030, such as a ring-like structure embedded in the distal shaft 4014. As noted elsewhere, the pull member 4028 may comprise any of a variety of materials and structures sufficient to transmit longitudinal forces along a length of the catheter body 4004. The pull member 4028 and the distal pull structure 4030 may be metallic, non-metallic or a combination thereof, including but not limited to stainless steel, Nitinol, nylon or other polymeric material. In some variations, the pull member 4028 may be coated, for example, to facilitate sliding in the pull lumen 4026, such as PTFE.

FIG. 14D depicts the proximal end 4030 of the steerable catheter 4000, comprising a rotatable knob 4032, a guide hub interface 4034, a hemostasis valve 4036 and a stopcock 4038. The knob 4032 may be configured to adjust the tension of the pull member 4028 by knob rotation, but in other variations, tension adjustment may occur by pulling the knob. Referring to FIG. 15E, the pull member 4028 may be attached to a hypotube 4040 by crimping, welding, adhesives or the like. The hypotube 4040 may be attached to a key structure 4042 which forms a complementary interfit with the knob 4032 to axially displace the pull member 4028 while permitting relative rotational movement between the knob 4032 and the key structure 4042. The key structure 4042 may also be axially secured to the knob 4032 using a screw 4044 or other attachment structure which permits relative rotational movement. In other variations, the knob may be configured to transmit rotational movement to the pull member.

An inner sleeve 4046 with an outer threaded surface 4048 may be attached to the base 4050 of the steering assembly. The outer threaded surface 4048 may interface with the inner threaded surface 4052 of the knob 4032. In some variations, to permit axial movement while restrict rotational movement of the pull member 4028, the hypotube 4040 or the key structure 4042 may be configured with a non-circular shape and/or one or more side protrusions which may resist rotational movement along an inner lumen 4054 of the inner sleeve 4046. For example, FIG. 14E depicts the inner lumen 4054 comprising an elongate groove 5056 which accommodates axial movement of the set screws 5058 attached to and protruding from the key structure 4042 while restricting rotational displacement of the screws 5058.

Figure 15A:
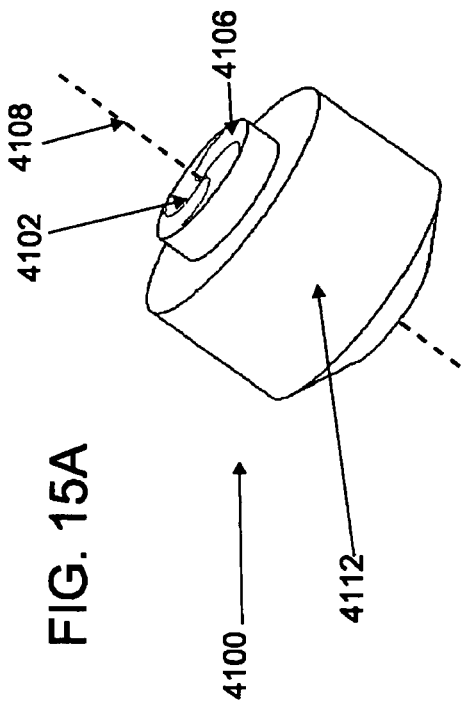
FIG. 15A is a perspective view of a variation of a hemostatic seal.
Figure 15B:
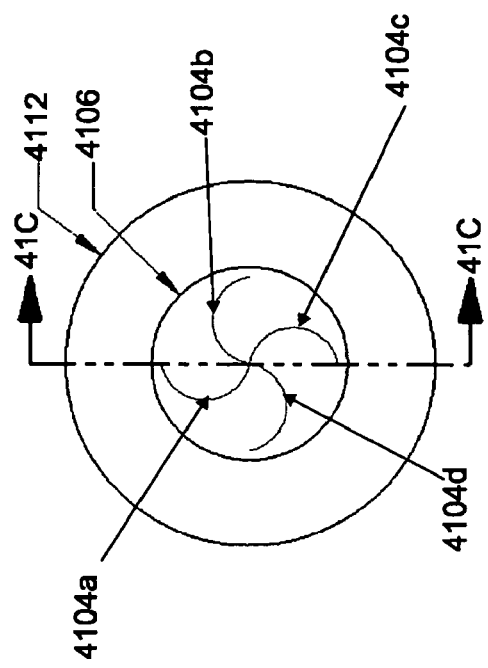
FIG. 15B is a posterior elevational view of the seal.
Figure 15C:
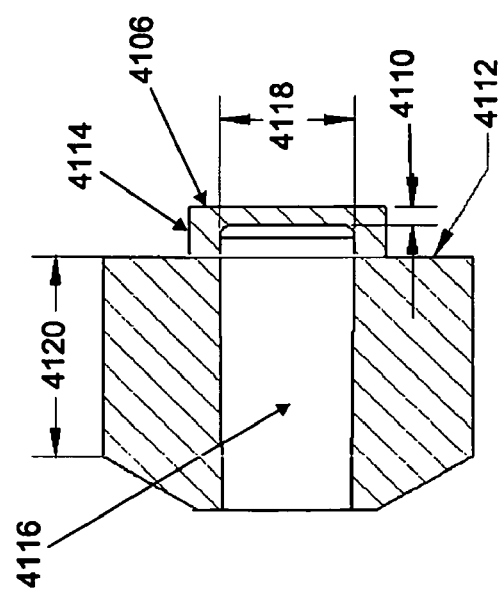
FIG. 15C is a cross-sectional view of the seal.
Figure 16:
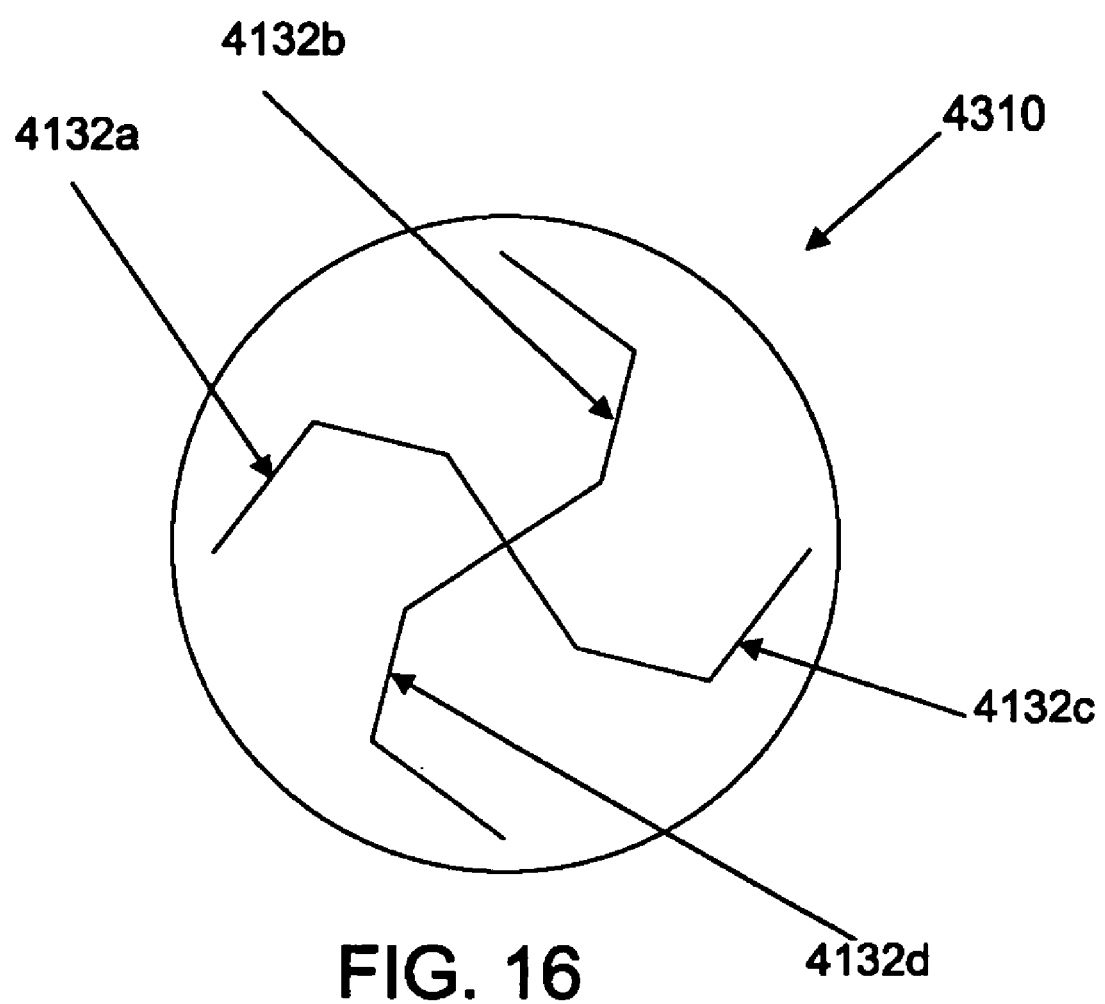
FIG. 16 is a posterior elevational view of another variation of a hemostatic seal.

To reduce the risk of blood or fluid leakage from the catheter 4000 during a procedure, the proximal end 4030 may further comprise a hemostasis valve or seal 5060 through which instruments may be inserted or withdrawn. The hemostatic seal may comprise any of a variety of configurations known in the art. In some examples, the hemostatic seal may comprise one or more slits on a septum or sealing member which forms one or more seal flaps. Upon insertion of an instrument or device through the sealing member, the seal flaps deform or deflect to permit passage of the device while exerting force around a perimeter of the device to substantially resist passage of fluid or gas through the sealing member. Referring to FIGS. 15A to 15C, in some examples, the sealing member 4100 has a seal opening 4102 comprising at least one non-linear slit 4104a-d with respect to the seal face 4106 or a transverse plane of the seal axis 4108. In the depicted example, the sealing opening 4102 comprises four arcuate or spiral-shaped slits 4104a-d arranged about the seal axis 4108. Each of the slits 4104a-d has the same relative shape and size as the other slits 4104a-d and uniformly spaced around the axis 4108, but in other examples, a different number of slits may be provided, one or more slits may have a different size or shape, the slits may be non-uniformly spaced or non-symmetrically arranged, and/or may intersect at location different from the center of the seal face 4106. In FIG. 16, for example, the sealing member 4130 comprises a plurality of multi-angled slits 4132a-d. Referring back to FIG. 14D, the hemostasis valve 4036 and the stopcock 4038 may be detached from the guide hub 4034 to permit direct insertion of instruments into the catheter 4000, or to attach other configurations of hemostasis seals, valves, connectors, sensors and the like.

Referring back to FIGS. 15A to 15C, the slits 4104a-d may have a generally orthogonal orientation through the seal face 4106, or may be angled or skewed. In some examples, the slits 4104a-d may be generally angled with respect to the seal face 4106 in the range of about 5 degrees to about 85 degrees, in some configurations about 10 degrees to about 60 degrees, and in other configurations about 20 degrees to about 45 degrees. The seal face 4106 or the seal member 4100 may comprise any of a variety of elastic or flexible materials, including any of a variety of silicones such as NuSil Med-4035, Med-4820, and MED50-5338, may have a durometer in the range of about 20 to about 80, in some examples about 15 to about 60, and in other examples about 20 to about 40. The thickness 4110 of the seal face 4106 may be in the range of about 0.01" to about 0.1", in some examples about 0.02" to about 0.05", and in other examples about 0.025" to about 0.03". As illustrated in FIG. 15B, the seal face 4106 may be raised or offset from the body 4112 of the sealing member 4100. The raised distance 4114 of raised seal face 4106 may be in the range of about 0.01" to about 0.2", in some configurations about 0.02" to about 0.1" and in other configurations about 0.04" to about 0.06".

The body 4112 may comprise a lumen 4116 in communication with the sealing opening 4102. The lumen 4116 may have a uniform or non-uniform diameter, cross-sectional area and/or cross-sectional shape. Lumens with non-uniform diameters may taper toward or away from the seal opening 4102, and the taper may be linear or non-linear. In some examples, the lumen 4116 may have an average diameter 4118 in the range of about 0.05" to about 0.5" or more, in some configurations about 0.1" to about 0.3", and in other configurations about 0.15" to about 0.2". The lumen 4116 may have a length 4120 anywhere in the range of about 0.1" to about 1" or more, in some configuration about 0.2" to about 0.5", and in other configurations about 0.25" to about 0.4". The body 4112 may have any of a variety of shapes, including cylindrical, frustoconical, box-like or other shapes, and may be coupled to the guide tunnel by a frame or housing.

As illustrated in FIGS. 13A to 13E, in one embodiment, guide catheter 112 is used to access the subvalvular region 116 for delivery of a cinchable implant. After passing a guidewire 118 through guide catheter 112 and along subvalvular region 116, a multi-window tunnel catheter 120 is passed down guidewire 118. In one embodiment, tunnel catheter 120 a releasable multi-window tunnel catheter as described in one or more embodiments of U.S. Pat. Appl. Ser. No. 61/026,697, entitled "MULTI-WINDOW GUIDE TUNNEL" filed on Feb. 6, 2008, which is herein incorporated by reference in its entirety. After guidewire 118 is removed from tunnel catheter 120, a delivery catheter (not shown) carrying one or more deployable anchors 122 coupled to a tether is secured to the subvalvular region 116. Embodiments of various devices usable with embodiments of the invention are described in U.S. patent application Ser. Nos. 10/656,797, 10/741,130, 10/792,681, 10/900,980, 10/901,555, 11/201, 949, 11/202,474, 11/232,190, 11/255,400, 11/270,034 and 11/583,627, which are incorporated by reference in their entirety.

In other embodiments, any of a variety of catheters and intralumenal instruments may be configured with one or more deformation zones. In addition to performing cinching of the subvalvular region about the mitral valve, these catheters and instruments may be used for other therapeutic and diagnostic procedures, including but not limited to access other cardiac valves (e.g. tricuspid valve, pulmonary valve and aortic valve), access to the coronary vasculatures, including the coronary arteries and coronary venous vasculature, including the coronary sinus, transseptal, transapical and other transmyocardial procedures, electrophysiological procedures, implantation of cardiac rhythm management devices, genitourinary procedures, gastrointestinal procedures including access to the hepatobiliary tree, cerebrovascular procedures including implantation of vascular coils, and others.

While this invention has been particularly shown and described with references to embodiments thereof, it will be understood by those skilled in the art that various changes in form and details may be made therein without departing from the scope of the invention. For all of the embodiments described above, the steps of the methods need not be performed sequentially.

What is claimed is:

1. A catheter, comprising:
   a deformation zone comprising a proximal end, a distal end, a longitudinal length and a longitudinal axis therebetween, a lower durometer segment located along an inner curve of the deformation zone, a higher durometer segment located along an outer curve of the deformation zone, and a first contiguous longitudinal interface between the lower durometer segment and the higher durometer segment, wherein the first interface has a length equal to or greater than the longitudinal length of the deformation zone;
   a post-deformation section distal to the deformation zone formed with a curve;
   a pull structure between the distal end of the deformation zone and the curve of the post-deformation section; and
   a pull wire engaging the pull structure, the pull wire moveable to control deflection of the deformation zone.

2. The catheter of claim 1, wherein the lower durometer segment comprises a polymeric material.

3. The catheter of claim 1, wherein the higher durometer segment comprises a polymeric material.

4. The catheter of claim 1, wherein the first interface has a non-linear configuration.

5. The catheter of claim 4, wherein the first interface comprises a zig-zag configuration.

6. The catheter of claim 4, wherein the first interface comprises intercalating portions of the lower durometer segment and the higher durometer segment.

7. The catheter of claim 1, wherein the deformation zone further comprises a second interface between the lower durometer segment and the higher durometer segment, wherein the second interface is separate from the first interface.

8. The catheter of claim 7, wherein the second interface has a length greater than the longitudinal length of the deformation zone.

9. The catheter of claim 1, wherein the deformation zone has a first configuration and a second configuration, wherein the second configuration has an increased bend compared to the first configuration.

10. The catheter of claim 9, wherein the second configuration is a curved configuration having a lesser curvature and a greater curvature, and wherein the lower durometer segment is located along the lesser curvature.

11. The catheter of claim 1, wherein the higher durometer segment has an angular width of at least about 45 degrees on an axial cross-section of the deformation zone.

12. The catheter of claim 11, wherein the lower durometer segment has an angular width of at least about 90 degrees on the axial cross-section of the deformation zone.

13. The catheter of claim 12, wherein the lower durometer segment has an angular width of at least about 180 degrees on the axial cross-section of the deformation zone.

14. A catheter, comprising:
   a deformation zone comprising a proximal end, a distal end, a longitudinal length therebetween, a first polymeric layer comprising a proximal edge, a distal edge, a first lateral edge and a second lateral edge, and a second polymeric layer comprising a proximal edge, a distal edge, a first lateral edge and a second lateral edge;

a post-deformation section distal to the deformation zone formed with a curve;

a pull structure between the distal end of the deformation zone and the curve; and a pull wire engaging the pull structure, the pull wire moveable to control deflection of the deformation zone;

wherein the first polymeric material has a lower durometer than the second polymeric material, and wherein the first polymeric material is located longitudinally along an inner curvature of the deformation zone and the second polymeric material is located longitudinally along an outer curvature of the deformation zone; and wherein the first lateral edge of the first polymeric layer is joined to at least a portion of the second lateral edge of the second polymeric layer; and wherein the second lateral edge of the first polymeric layer is joined to at least a portion of the first lateral edge of the second polymeric layer.

* * * * *